United States Patent [19]

Day et al.

[11] 4,152,450

[45] May 1, 1979

[54] 9-AMINO-DIBENZOPYRANS

[75] Inventors: William A. Day; Edward R. Lavagnino, both of Indianapolis, Ind.

[73] Assignee: Eli Lilly and Company, Indianapolis, Ind.

[21] Appl. No.: 878,844

[22] Filed: Feb. 17, 1978

[51] Int. Cl.$^2$ .................. A61K 31/35; A61K 31/455; C07D 311/80; A61K 31/42
[52] U.S. Cl. .................................... 424/283; 424/274; 424/267; 424/248.57; 424/248.55; 260/345.3; 260/326.8; 544/150; 546/196
[58] Field of Search .................. 260/345.3; 424/283, 424/274, 267, 248.57, 248.55

[56] References Cited

U.S. PATENT DOCUMENTS

| | | | |
|---|---|---|---|
| 3,649,650 | 3/1972 | Razdan et al. | 260/345.3 |
| 3,676,462 | 7/1972 | Pars et al. | 260/345.3 |

*Primary Examiner*—Nicky Chan
*Attorney, Agent, or Firm*—Charles W. Ashbrook; Arthur R. Whale

[57] ABSTRACT

1-Hydroxy-3-substituted-tetrahydro and hexahydrodibenzo[b,d]pyrans having an amino group or amino derivative at the 9-position are useful as analgesics, anti-depressants, anti-anxiety agents, hypotensive agents, and intermediates. Pharmaceutical formulations containing such 9-amino derivatives are provided, as well as a method of treating hypertension.

18 Claims, No Drawings

9-AMINO-DIBENZOPYRANS

BACKGROUND OF THE INVENTION

A number of dibenzopyran compounds recently have been found to be useful in the treatment of depression, pain and anxiety. U.S. Pat. Nos. 3,928,598, 3,944,673 and 3,953,603 describe various hexahydro-dibenzo[b,d]pyran-9-ones which have such utilities. Particular attention is drawn to dl-trans-1-hydroxy-3-(1,1-dimethylheptyl)-6,6-dimethyl-6,6a,7,8,10,10a-hexahydro-9H-dibenzo[b,d]pyran-9-one, now generically referred to as nabilone.

Several modifications of known dibenzopyran compounds have been made in an effort to discover new compounds having enhanced pharmacological usefulness or new utilities altogether. Only a few of such modifications have included the incorporation of nitrogen in the dibenzo-pyran molecule. U.S. Pat. No. 3,886,184 describes certain 1-amino-3-alkyl-9-alkyl-dibenzo[b,d]pyrans. U.S. Pat. No. 3,676,462 discloses a number of 1-aminoalkyl and 3-aminoalkyl dibenzo[b,d]pyrans. Similarly, nitrogen has been incorporated into the C-ring of certain dibenzo[b,d]pyran-type compounds. U.S. Pat. No. 3,878,219 discloses dibenzo[b,d]pyrans having a nitrogen atom in the C-ring at the 9-position. U.S. Pat. No. 3,888,946 discloses similar nitrogen containing heterocycles wherein the C-ring is five membered rather than six.

SUMMARY OF THE INVENTION

The present invention is directed to dibenzo[b,d]pyrans having a nitrogen atom attached directly to the 9-position carbon atom. The invention resides in the concept of a class of compounds known generically as 9-amino-dibenzo[b,d]pyrans. The invention is more particularly directed to tetrahydro and hexahydro dibenzo[b,d]pyrans having the general formula

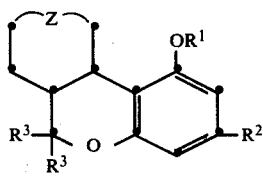

wherein:
$R^1$ is hydrogen or $C_1-C_4$ alkanoyl;
$R^2$ is $C_5-C_{10}$ alkyl or $C_5-C_{10}$ alkenyl;
$R^3$ is hydrogen or methyl; and
Z is selected from the group consisting of

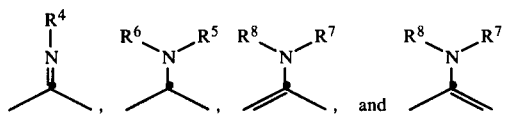

wherein:
$R^4$ is hydroxy, $C_1-C_4$ alkoxy, or $C_1-C_7$ alkanoyloxy;
$R^5$ taken singly is hydrogen, hydroxy, $C_1-C_4$ alkoxy, $C_1-C_4$ alkyl, $CH_2C_2-C_4$ alkenyl, $CH_2C_2-C_4$ alkynyl, $C_1-C_7$ alkanoyl, $C_1-C_7$ alkanoyloxy, phenyl-$C_1-C_2$ alkyl, phenyl-$C_1-C_2$ alkanoyl, —$(CH_2)_n$—OH, —$(CH_2)_n$—O—$C_1$—$C_2$ alkanoyl,

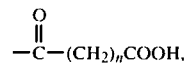

wherein n is 2, 3 or 4;
$R^6$ taken singly is hydrogen, $C_1-C_4$ alkyl, $CH_2C_2-C_4$ alkenyl, $CH_2C_2-C_4$ alkynyl, $C_1-C_7$ alkanoyl, phenyl-$C_1-C_2$ alkyl or phenyl-$C_1-C_2$ alkanoyl, $R_5$ and $R_6$ taken together with the nitrogen atom to which they are attached complete a heterocyclic ring selected from pyrrolidine, 2-oxopyrrolidine, 2,5-dioxopyrrolidine, piperidine, 2-oxopiperidine, 2,6-dioxopiperidine and morpholine;

$R^7$ taken singly is hydrogen, $C_1-C_7$ alkanoyl, phenyl-$C_1-C_2$ alkanoyl or

wherein n is 2, 3 or 4;
$R^8$ taken singly is $C_1-C_7$ alkanoyl or phenyl-$C_1-C_2$ alkanoyl; and
$R^7$ and $R^8$ taken together with the nitrogen atom to which they are attached complete a heterocyclic ring selected from 2-oxopyrrolidine, 2,5-dioxopyrrolidine, 2-oxopiperidine and 2,6-dioxopiperidine,
and the non-toxic pharmaceutically acceptable acid addition salts and quaternary ammonium salts thereof.

A preferred group of compounds according to this invention are those having the above formula wherein:
$R^1$ is hydrogen;
$R^3$ is methyl; and
Z is a group of the formula

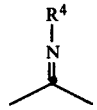

wherein $R^4$ has the above defined meaning, and is preferably hydroxy or $C_1-C_4$ alkoxy, especially methoxy.

A further preferred group of compounds are represented by the above formula wherein:
$R^1$ is hydrogen or $C_1-C_4$ alkanoyl;
$R^3$ is methyl; and
Z is a group of the formula

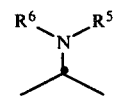

wherein $R^5$ and $R^6$ have the above-defined meanings, but are most preferably hydrogen, alkyl, alkenyl, or $C_1-C_7$ alkanoyl.

Another preferred group of compounds comprehended by this invention have the above formula wherein:
$R^1$ is hydrogen and Z is a group of the formula

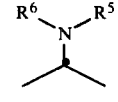

wherein $R^5$ is hydrogen and $R^6$ is $C_1-C_7$ alkanoyl, especially $C_1-C_2$ alkanoyl.

Still another preferred group of compounds are those having the above formula wherein Z is selected from

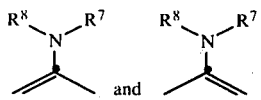

and in which $R^7$ preferably is hydrogen or $C_1$-$C_7$ alkanoyl.

A group of compounds especially suited as intermediates in the preparation of other compounds of the invention are those defined by the above general formula wherein Z is

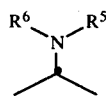

and $R^5$ and $R^6$ both are hydrogen.

A further aspect of this invention is a pharmaceutical formulation comprising one or more of the biologically active compounds of the above general formula in combination with a suitable pharmaceutical carrier, diluent, or excipient therefor. The formulations provided by this invention are particularly useful in treating mammals suffering from hypertension. The formulations also can be utilized in the treatment of anxiety, depression and related central nervous system disorders. The formulation can also be used in the treatment of glaucoma.

An additional embodiment of this invention is a method of treating hypertension comprising administering to an animal suffering from hypertension and in need of treatment an amount sufficient to lower blood pressure of a hypotensively active compound of the above formula. A preferred method of treatment according to this invention comprises administering a dose effective for lowering blood pressure of a compound having the above formula wherein $R^6$ and $R^7$ are $C_1$-$C_7$ alkanoyl, especially $C_1$-$C_2$ alkanoyl.

DETAILED DESCRIPTION OF THE INVENTION

In the above formula representing the 9-amino-dibenzo[b,d]pyrans provided by this invention, $R^1$ is defined as hydrogen and $C_1$-$C_4$ alkanoyl. The term "$C_1$-$C_4$ alkanoyl" as used herein refers to an acyl residue of a carboxylic acid having from 1 to 4 carbon atoms. Examples of such $C_1$-$C_4$ alkanoyl groups include formyl, acetyl, propionyl, n-butyryl, and isobutyryl.

$R^2$ is defined as a $C_5$-$C_{10}$ alkyl group and a $C_5$-$C_{10}$ alkenyl group. Such terms take on the meaning assigned to them throughout the chemical art relating to dibenzopyrans. Examples of "$C_5$-$C_{10}$ alkyl" groups include both straight and branched chain alkyl groups such as n-pentyl, n-hexyl, n-heptyl, 1,1-dimethylheptyl, 1,2-dimethylheptyl, 1-ethyloctyl, 1,1-dimethyloctyl, 1,2,3-trimethylheptyl, 1-propylhexyl, isooctyl, n-decyl, and the like. The term "$C_5$-$C_{10}$ alkenyl" similarly refers to straight and branched alkenyl chains known in the art, examples of which include 2-pentenyl, 3-hexenyl, 5-heptenyl, 1,1-dimethyl-2-heptenyl, 1,2-dimethyl-1-heptenyl, 2,3-dimethyl-2-heptenyl, 1-ethyl-2-octenyl, 2-ethyl-1-heptenyl, 2-decenyl, 1-nonenyl, 1-methyl-1-nonenyl, and related alkenyl groups.

As noted in the above generic formula representing the compounds of this invention, Z can be an imino containing moiety representing by the formula

in which $R^4$ is hydroxy, $C_1$-$C_4$ alkoxy, or $C_1$-$C_7$ alkanoyloxy. It will of course be recognized that compounds of the invention having such definition for Z are oximes, O-alkyl oximes and O-acyl oximes. Typical $C_1$-$C_4$ alkoxy groups which go to make up such O-alkyl oximes include methoxy, ethoxy, n-propoxy and isobutoxy. Examples of $C_1$-$C_7$ alkanoyloxy groups include formyloxy, acetoxy, propionoxy and isobutyroxy.

The term Z similarly is defined as a group having the formula

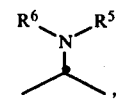

In such groups, $R^5$ includes $C_1$-$C_4$ alkoxy groups such as methoxy, ethoxy and n-butoxy. Both $R^5$ and $R^6$ as defined include $C_1$-$C_4$ alkyl groups such as methyl, ethyl, n-propyl, isopropyl and n-butyl. Examples of $CH_2C_2$-$C_4$ alkenyl groups include 2-pentenyl, 2-propenyl and 3-butenyl. Similarly, $CH_2C_2$-$C_4$ alkynyl refers to groups such as 2-propynyl, 2-butynyl and 1-methyl-2-propynyl. The groups $R^5$ and $R^6$ additionally are defined as "$C_1$-$C_7$ alkanoyl". Such definition refers to acyl residues of carboxylic acids having from 1 to 7 carbon atoms. Such groups can be straight or branched chain acyl groups. Typical $C_1$-$C_7$ alkanoyl groups include formyl, acetyl, propionyl, isobutyryl, pentanoyl, isohexanoyl, 3-ethylpentanoyl, 2-methylhexanoyl, 1,2-dimethylpentanoyl, and related groups. Preferred alkanoyl groups are $C_1$-$C_4$ alkanoyl, and most preferred are $C_1$-$C_2$ alkanoyl. $R^5$ and $R^6$ also include phenyl-$C_1$-$C_2$ alkyl groups such as benzyl and 2-phenethyl, as well as phenyl-$C_1$-$C_2$ alkanoyl such as benzoyl and phenylacetyl. $R^5$ can additionally be a group having the formula $-(CH_2)_n-OH$, wherein n is 2, 3 or 4. Such groups include 2-hydroxyethyl, 3-hydroxypropyl and 4-hydroxybutyl. The hydroxy group of such moieties can be acylated with a $C_1$-$C_2$ alkanoyl group thereby providing substituents such as acetoxymethyl and the like. When $R^5$ defines the group $-CO(CH_2)_nCOOH$, such groups include 3-(hydroxycarbonyl)propionyl, 4-(hydroxycarbonyl)butyryl, and 5-(hydroxycarbonyl)pentanoyl.

Many of the compounds provided by this invention are amines which are of such basic nature that they readily form acid addition salts and quaternary ammonium salts. For example, a 9-amino, 9-alkylamino or 9-dialkylamino-dibenzo[b,d]pyran of this invention can exist as a free base or alternatively as a salt. Non-toxic pharmaceutically acceptable salts contemplated by this invention are salts which do not add substantial toxicity to the parent amine and consequently can be utilized pharmaceutically in a manner similar to the free amine bases. The acid addition salts of this invention are formed by standard procedures such as reacting the basic amine with an organic or inorganic acid. Acids commonly used to form non-toxic pharmaceutically acceptable acid addition salts include mineral acids such as hydrochloric acid, hydrobromic acid, sulfuric acid, phosphoric acid, as well as acids such as sulfamic acid, nitric acid and nitrous acid. Typically useful organic acids include acetic acid, oxalic acid, lactic acid, ascorbic acid, maleic acid, fumaric acid, succinic acid, p-toluene-sulfonic acid, benzoic acid, methanesulfonic acid, adipic acid, and the like.

In similar fashion the basic amines of this invention which are tertiary amines readily form quaternary ammonium salts which also are pharmaceutically acceptable. Such tertiary amines are quaternized by reaction with an alkylating agent such as methyl iodide, ethyl bromide, n-butyl chloride, isopropyl iodide, allyl bromide, dimethylsulfate and the like. It will of course be recognized that salts of compounds such as amides and oximes normally are not formed since the nitrogen atom is not sufficiently basic in nature, and quaternary ammonium salts are formed only when both $R^5$ and $R^6$ of the above formula are groups such as alkyl, alkenyl, phenylalkyl, and the like.

The 9-amino-dibenzo[b,d]pyrans provided by this invention can be prepared by any of a number of methods. Routinely, there is first prepared an oxime derivative which is then reduced to afford an N-unsubstituted 9-amino-dibenzopyran compound, which then can be further derivatized as desired by normal procedures such as alkylation and acylation. The starting materials utilized in the synthesis of the oximes are hydroxyl amine and alkoxy amines such as methoxy amine, and a 9-keto dibenzo[b,d]pyran derivative. These dibenzo[b,d]pyran-9-one starting materials are represented by the general formula

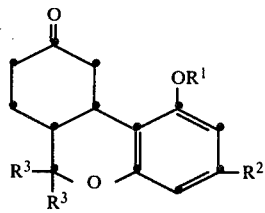

wherein $R^1$, $R^2$ and $R^3$ are as defined hereinabove. The dibenzopyran-9-one compounds which are preferably utilized in the preparation of the oximes of this invention are those of the above formula wherein $R^1$ is hydrogen. Such compounds are included in the following list of representative starting materials:

1-hydroxy-3-n-pentyl-6,6-dimethyl-6,6a,7,8,10,10a-hexahydro-9H-dibenzo[b,d]pyran-9-one;

1-hydroxy-3-n-octyl-6,6-dimethyl-6,6a,7,8,10,10a-hexahydro-9H-dibenzo[b,d]pyran-9-one;

1-hydroxy-3-(1,2-dimethylheptyl)-6,6a,7,8,10a,10a-hexahydro-9H-dibenzo[b,d]pyran-9-one;

1-hydroxy-3-(1,2-dimethyl-1-heptenyl)-6,6-dimethyl-6,6a,7,8,10,10a-hexahydro-9H-dibenzo[b,d]pyran-9-one;

1-hydroxy-3-(1-ethylhexyl)-6,6-dimethyl-6,6a-7,8,10,10a-hexahydro-9H-dibenzo[b,d]pyran-9-one;

1-hydroxy-3-(1,1-dimethylheptyl)-6,6a,7,8,10,10a-hexahydro-9H-dibenzo[b,d]pyran-9-one;

1-hydroxy-3-(1,2,3-trimethyl-2-pentenyl)-6,6-dimethyl-6,6a,7,8,10,10a-hexahydro-9H-dibenzo[b,d]pyran-9-one; and related compounds.

It should be recognized that since the above-described starting ketones are dibenzo[b,d]pyrans which are totally saturated in the C-ring, stereochemical isomers at the 6a and 10a carbon atoms exist. More specifically, the starting ketones, and consequently the 9-amino-dibenzo[b,d]pyrans of this invention, can exist as 6a,10a-cis-isomers and as 6a,10a-trans isomers. Each of these isomers constitute a racemic or dl pair. For example, a 6a,10a-cis derivative can have both the 6a-hydrogen atom and the 10a-hydrogen atom oriented above the plane of the ring, or alternatively both hydrogen atoms can be oriented below the plane of the ring. These two isomers form a cis-dl racemic mixture. Similarly, a 6a,10a-trans isomer can be a compound wherein the 6a-hydrogen atom is above the plane of the ring while the 10a-hydrogen atom is oriented below, or alternatively the 6a-hydrogen atom can be oriented below the plane of the ring and the 10a-hydrogen atom oriented above. Again, these two isomers constitute a trans-dl pair. Normally, the preparation of the compounds of this invention comprehends utilizing a racemic mixture of either a 6a,10a-cis-hexahydrodibenzo[b,d]pyranone, i.e., a dl-cis isomer, or alternatively a racemic mixture of a 6a,10a-trans-isomer, i.e., a dl-trans-hexahydrodibenzo[b,d]pyranone. It should be noted, however, that the compounds of this invention can also be derived from our optically active d or l-cis ketone or d or l-trans ketone, thereby giving the corresponding 9-amino-dibenzo[b,d]pyran having the same stereochemical integrity as the starting ketone. Since all of the individual stereochemical isomers at the 6a and 10a positions appear to possess useful pharmacological activity, it is often preferable to simply utilize as a starting material a mixture of dl-cis and dl-trans hexahydrodibenzo[b,d]pyran-9-ones. It is especially convenient to utilize such racemic mixtures since these are readily available synthetically. Examples of such preferred starting materials include:

dl-trans-1-hydroxy-3-(1,2-dimethylheptyl)-6,6-dimethyl-6,6a,7,8,10,10a-hexahydro-9H-dibenzo[b,d]pyran-9-one;

dl-trans-1-hydroxy-3-(n-octyl)-6,6-dimethyl-6,6a,7,8,10,10a-hexahydro-9H-dibenzo[b,d]pyran-9-one;

dl-cis-1-hydroxy-3-(n-decyl)-6,6a,7,8,10,10a-hexahydro-9H-dibenzo[b,d]pyran-9-one; and dl-cis-1-hydroxy-3-(1,2-dimethylhexyl)-6,6-dimethyl-6,6a,7,8,10,10a-hexahydro-9H-dibenzo[b,d]pyran-9-one.

The various dibenzopyranone starting materials required to prepare the compounds of this invention are either known in the art or are readily preparable by methods taught in the art. For example, a large number of dl-cis and dl-trans-hexahydrodibenzo[b,d]pyran-9-ones are disclosed in U.S. Pat. Nos. 3,928,598, 3,944,673 and 3,953,603. The preparation of dl-cis and dl-trans-hexahydrodibenzo[b,d]pyran-9-ones is additionally described in U.S. Pat. Nos. 3,507,885 and 3,636,058. The synthesis of the various starting materials utilized in the preparation of the compounds of this invention is further described in detail by Archer et al., in a paper entitled "Cannabinoids 3. Synthetic Approaches to 9-Ketocannabinoids. Total Synthesis of Nabilone", *J. Org. Chem.*, 42, No. 13, pp. 2277–2284, (1977).

As hereinbefore pointed out, the oximes and alkoxy oximes of this invention (ie. where $R^4$ is hydroxy or $C_1$-$C_4$ alkoxy) can be prepared by reacting a hexahydro-dibenzo[b,d]pyran-9-one with hydroxyl amine or an alkoxy amine such as methoxy amine and ethoxy amine. Such amines generally are commercially available in the form of an acid addition salt, and can be utilized by adding a base to the reaction mixture to liberate the free amine in situ or by neutralizing the salt prior to employing the free amine in the reaction. In preparing the oximes and O-alkyl oximes of this invention, a dibenzo[b,d]pyran-9-one and the hydroxyl amine or alkoxy amine are typically reacted in approximately equimolar quantities, and the reaction is best conducted in a mutual solvent such as methanol, ethanol, water, or a mixture of such solvents. The reaction generally is substantially complete after about ½ to 4 hours when carried out at a temperature in the range from about 25° to about 100° C. The product oxime or O-alkyl oxime is conveniently isolated by simply diluting the reaction mixture with water or aqueous acid, and then extracting the oxime into a water immiscible solvent such as diethyl ether, benzene, chloroform, dichloromethane, ethyl acetate, or the like. Evaporation of the solvent from the organic extracts normally leaves the product oxime as an oil or solid, which generally can then be crystallized if desired from solvents such as n-hexane and petroleum ether. Examples of oxime derivatives thus prepared include:

1-hydroxy-3-n-pentyl-6,6-dimethyl-9-hydroxyimino-6a,7,8,9,10,10a-hexahydro-6H-dibenzo[b,d]pyran;

1-hydroxy-3-(1,2-dimethyl-2-pentenyl)-9-methoxyimino-6a,7,8,9,10,10a-hexahydro-6H-dibenzo[b,d]pyran;

dl-trans-1-hydroxy-3-(1,2-dimethylheptyl)-9-ethoxyimino-6a,7,8,9,10,10a-hexahydro-6H-dibenzo[b,d]pyran; and dl-cis-1-hydroxy-3-(1,1-dimethyloctyl)-6,6-dimethyl-9-isobutoxyimino-6a,7,8,9,10,10a-hexahydro-6H-dibenzo[b,d]pyran.

The oxime derivatives so formed are useful as pharmacological agents in addition to being valuable as intermediates. For example, reduction of such compounds provides hydroxy amine derivatives and alkoxy amine derivatives. Additionally, the hydroxyimino compounds can be O-alkylated with $C_1$-$C_4$ alkylating agents such as isobutyl bromide to afford the corresponding 9-alkoxyimino-dibenzo[b,d]pyrans. Furthermore, normal acylation of the hydroxyimino compounds, for instance by reaction with a $C_1$-$C_7$ carboxylic acid acylating agent, provides the corresponding 9-alkanoyloxyimino-hexahydrodibenzopyran derivatives.

Reduction of the imino derivatives thus formed to afford 9-amino and 9-substituted amino derivatives can be accomplished in any of a number of ways. Commonly used reducing agents include diborane, sodium borohydride, sodium cynaoborohydride and lithium aluminum hydride. Catalytic hydrogenation also can be utilized if desired. Such reductions typically are carried out in an organic solvent such as an alcohol, especially methanol or ethanol, or aromatic hydrocarbons such as benzene and toluene. Reduction of the oxime i.e., a 9-hydroxyimino derivative, to provide the corresponding 9-hydroxyamino compound normally is complete within about six to twenty hours when carried out at about 25° C. Of course it will be recognized that reduction of a 9-alkoxyimino derivative affords the corresponding 9-alkoxyamino compound. For instance, reduction of a compound such as 1-hydroxy-3-n-decyl-6,6-dimethyl-9-ethoxyimino-6a,7,8,9,10,10a-hexahydro-6H-dibenzo[b,d]pyran by reaction with sodium borohydride in ethanol affords the corresponding 9-ethoxyamino-dibenzo[b,d]pyran. Such compounds are easily isolated by simply removing the reaction solvent, for example by evaporation. The product can be further purified if desired by routine methods such as chromatography and crystallization.

Like the hydroxyimino compounds previously mentioned, the hydroxyamino derivatives are readily acylated by reaction with a $C_1$-$C_7$ alkanoic acid acylating agent to provide the corresponding 9-($C_1$-$C_7$ alkanoyloxy)aminodibenzopyrans of this invention.

9-Unsubstituted-amino-dibenzo[b,d]pyrans provided by this invention, i.e., hexahydrodibenzopyrans having an $NH_2$ group at the 9-position, can be prepared by exhaustive reduction of the aforementioned 9-hydroxyimino derivatives, or by further reduction of the 9-hydroxyamino compounds. For example, further reduction of a 9-hydroxyamino derivative can be effected by reaction with zinc and acetic acid or sodium in liquid ammonia, as well as by catalytic hydrogenation. The preferred procedure, however, is to simply reduce a 9-hydroxyimino derivative by any one of several available methods. For example, reaction of a compound such as 1-hydroxy-3-(1,2-dimethylheptyl)-9-hydroxyimino-6a,7,8,9,10,10a-hexahydro-6H-dibenzo[b,d]pyran with hydrogen in the presence of a catalyst such as Raney nickel effects complete reduction to afford the primary amine, for example, 1-hydroxy-3-(1,2-dimethylheptyl)-9-amino-6a,7,8,9,10,10a-hexahydro-6H-dibenzo[b,d]pyran. Such hydrogenation reactions typically are carried out in a solvent such as methanol and liquid ammonia, and normally are complete in about four to eight hours when conducted at an elevated temperature of about 80° to 120° C. The hydrogen atmosphere generally is maintained at about 500 to 1500 psi. The product, a primary amine, can be recovered by simply filtering the reaction mixture and evaporating the solvent. Further purification of the amine can be accomplished if desired by general methods such as crystallization, acid addition salt formation, chromatography, and the like.

The primary 9-amino-hexahydro-dibenzo[b,d]pyrans thus formed, while effecting the central nervous system in animals, are particularly important intermediates leading to other compounds of the invention. Alkylation of the primary 9-amino group, for example, affords the corresponding N-alkyl and N,N-dialkylamino-hexahydro-dibenzo[b,d]pyrans. Acylation provides the corresponding N-acyl and N,N-diacylamino-hexahydro-dibenzo[b,d]pyrans of the invention.

Alkylation of a 9-amino-hexahydro-dibenzopyran can be accomplished by reaction of the amino derivative with an alkylating agent according to standard procedures. As used herein, the term "alkylating agent" includes, in addition to reagents having a $C_1$-$C_4$ alkyl group, those reagents having a $CH_2C_2$-$C_4$ alkenyl group, a $CH_2C_2$-$C_4$ alkynyl group, a phenyl-$C_1$-$C_2$ alkyl group, as well as $-(CH_2)_n-OH$ alkylating agents. Typical examples of such alkylating agents include alkyl halides such as methyl iodide, ethyl bromide, propyl bromide, isobutyl iodide, 3-butenyl bromide, 2-propenyl bromide, 2-hydroxyethyl iodide; alkyl sulfates, for example, dimethyl sulfate, diisopropyl sulfate, diallyl sulfate, and di-3-butynyl sulfate. Other alkylating agents commonly used include tosylates such as benzyl tosylate, 2-phenylethyl tosylate, tert.-butyl tosylate, 3-butenyl tosylate, 2-butynyl tosylate; and the like.

In order to effect mono-alkylation of a primary 9-amino-hexahydro-dibenzo[b,d]pyran, the reactants typically are commingled in approximately equimolar quantities. Excessive alkylating agent is utilized in order to effect dialkylation, where it is desired that $R^5$ and $R^6$ in the above formula are the same alkyl, alkenyl, alkynyl, hydroxyalkyl or phenylalkyl moiety. The reaction is best carried out in the presence of a suitable base to act as an acid scavenger. Bases commonly utilized include triethylamine, benzylamine, sodium hydroxide, pyridine, sodium methoxide, sodium carbonate, and related bases. The reaction is best carried out in a non-reactive organic solvent such as an ether, for instance diethyl ether, diisopropyl ether, methyl ethyl ether and dioxane. Other commonly used solvents include alcohols such as methanol, ethanol, isopropanol; halogenated hydrocarbons such as dichloromethane and chloroform; and aromatic solvents such as benzene, toluene, xylene and the like. The reaction generally is complete within about two to twenty hours when carried out at a temperature ranging from about 30° to 150° C. The product of the alkylation reaction, a 9-alkylamino or dialkylamino dibenzo[b,d]pyran derivative, is readily isolated by simply removing the solvent from the reaction mixture and washing the product with water or dilute acid. The product so formed can then be further purified if desired by chromatography or crystallization. Alternatively, the 9-amino derivative can be isolated as a salt, which characteristically is highly crystalline and can be isolated by filtration. In particular, the reaction mixture containing the alkylated or dialkylated amine can be acidified by the addition of an acid such as hydrochloric acid or succinic acid, thereby converting the amine to an acid addition salt. In the case of a N,N-dialkylamine, prepared according to the above described process, i.e., those compounds wherein $R^5$ and $R^6$ both are selected from alkyl, alkenyl, alkynyl, phenylalkyl, and the like, such compounds if desired can be converted to a quaternary ammonium salt by further reaction with an alkylating agent such as methyl bromide, allyl iodide or propargyl bromide. Such quaternary ammonium salts are highly crystalline solids and subject to ready recrystallization.

It will of course be recognized that once a 9-amino-dibenzopyran is mono-alkylated according to the above-described process to provide a compound of the invention wherein $R^5$ is alkyl, alkenyl, alkynyl hydroxylalkyl or phenylalkyl and $R^6$ is hydrogen, that further alkylation can be effected by reaction with an alkylating agent in a manner similar to that described above. Such alkylation reaction can provide dialkylated 9-amino-dibenzo[b,d]pyrans of this invention wherein the alkyl groups are dissimilar, i.e. $R^5$ and $R^6$ independently are alkyl, alkenyl, alkynyl, hydroxyalkyl, phenylalkyl and the like.

An alternative method for preparing the 9-alkylamino and dialkylamino-hexahydro-dibenzo[b,d]-pyrans of this invention comprises reductive alkylation of a ketone, i.e., reacting a hexahydro-dibenzo[b,d]pyran-9-one with a primary or secondary amine in the presence of a reducing agent. Commonly used amines include methylamine, diethylamine, 2-propenylamine, pyrrolidine, piperidine, morpholine, 3-butynylamine, N-methyl-3-butenylamine, 3-hydroxypropylamine, benzylamine, N-methyl-2-phenylethylamine, N-isopropylisobutylamine, dimethylamine and the like. The reaction generally is carried out by commingling approximately equimolar quantities of the dibenzopyran-9-one derivative and the amine in a solvent such as methanol or ethanol. A reducing agent such as hydrogen and a suitable catalyst, for example, sodium borohydride or sodium cyanoborohydride, are utilized in the reaction in order to effect complete reduction of the intermediate imine which is formed, thus providing the corresponding alkyl or dialkylamine dibenzopyran of this invention. Such reductive alkylation typically is carried out at a temperature of about 10° to 50° C. and normally is complete within about twelve to seventy-two hours. The product amine can be isolated as a free base or alternatively as an acid addition salt. Additional purification usually is accomplished by chromatography or crystallization.

As previously mentioned, the primary 9-aminohexahydro-dibenzo[b,d]pyrans can be acylated with any of a number of acylating agents to provide the various 9-amido derivatives of this invention, including compounds of the above formula wherein $R^5$ is $C_1-C_7$ alkanoyl. Reaction of a 9-(NH$_2$)-dibenzopyran with an acylating agent under relatively mild conditions effects mono-acylation to provide a 9-amido-hexahydro-dibenzo[b,d]pyran ($R^5$ is alkanoyl and $R^6$ is hydrogen). Such "relatively mild conditions" includes utilizing the acylating agent and the 9-amino-dibenzopyran in approximately equimolar quantities and carrying out the reaction at a temperature of about 0° to 50° C. Typically a base such as triethylamine or pyridine is utilized in the reaction as an acid scavenger. Commonly used acylating agents include $C_1-C_7$- and phenyl-$C_1-C_2$ alkanoic acid halides, azides, anhydrides, including mixed anhydrides, as well as cyclic anhydrides such as succinic anhydride, glutaric anhydride and adipic anhydride. Use of such cyclic anhydrides provides the amides of this invention wherein the acyl group has the formula $-CO(CH_2)_nCOOH$. Preferred acylating agents include acid halides and acid anhydrides. Examples of such reagents include acetyl chloride, propionic anhydride, formyl acetic anhydride, benzoyl chloride, phenylacetyl bromide, heptanoyl iodide, succinic anhydride and isobutyric anhydride. The acylation can be conducted in any of a number of organic solvents if desired, including alcohols such as methanol and ethanol, halogenated hydrocarbons such as dichloromethane and 1,2-dibromoethane, ethers such as diisopropyl ether, diethylether and tetrahydrofuran, as well as aromatic solvents such as benzene and toluene.

Under the "relatively mild conditions", monoacylation is usually complete within about four to about seventy-two hours to provide a 9-acylamino-hexahydro-dibenzopyran. For example, reaction of dl-cis-1-hydroxy-3-n-octyl-9-amino-6a,7,8,9,10,10a-hexahydro-6H-dibenzo[b,d]pyran with about one equivalent of isobutyryl chloride in benzene, in the presence of about one equivalent of a base such as pyridine, at about 25° C. for four hours, effects mono-acylation to provide dl-cis-1-hydroxy-3-n-octyl-9-isobutyramido-6a,7,8,9,10,10a-hexahydro-6H-dibenzo[b,d]pyran. The product, a 9-acylamino-dibenzo[b,d]pyran, is readily isolated by simply diluting the reaction mixture with water and then extracting the product therefrom into a suitable water immiscible solvent such as diethyl ether, chloroform, dichloromethane, or the like. Removal of the solvent from the extracts, for instance by evaporation under reduced pressure, affords the corresponding 9-acylamino-dibenzo[b,d]pyran, which compound can be further purified if desired by standard methods such as chromatography and crystallization.

The 9-acylamino-dibenzopyrans wherein the acyl group has the formula $-CO(CH_2)_nCOOH$ are useful both as intermediates and as pharmacological agents. Conversion of such compounds to acid halides and reaction of such acid halides with a strong base such as sodium hydride effects cyclization to provide compounds of the above formula wherein $R^5$ and $R^6$ complete a heterocyclic ring such as 2,5-dioxopyrrolidine and 2,6-dioxopiperidine.

Exhaustive acylation of 9-amino and 9-acylaminodibenzo[b,d]pyrans effects peracylation to afford 1-acyloxy-9-diacylamino-hexahydro-dibenzo[b,d]pyrans. Such peracylation can be effected by reacting either a 9-amino or a 9-acylamino-hexahydro-dibenzo[b,d]pyran with an excess of an acylating agent, for example from about 2 to 10 molar excess, as well as carrying out the reaction at an elevated temperature of about 60° to about 150° C. The peracylation is carried out in the presence of a strong base such as sodium hydride. As an illustration of peracylation, a compound such as dl-cis-1-hydroxy-3-(2-hexenyl)-9-acetamido-6a,7,8,9,10,10a-hexahydro-6H-dibenzo[b,d]pyran can be reacted with about a 5 molar excess of propionyl bromide in the presence of sodium hydride at about 100° C. for about seventy-two hours to afford dl-cis-1-propionoxy-3-(2-hexenyl)-9-(N-propionyl)acetamido-6a,7,8,9,10,10a-hexahydro-6H-dibenzo[b,d]pyran.

The tri-acylated hexahydro-dibenzopyrans of this invention can easily be hydrolyzed by reaction with an aqueous base such as sodium hydroxide or potassium carbonate to afford a mono-acylated derivative, namely a 9-acylamino-hexahydro-dibenzo[b,d]pyran.

Diacylated compounds of this invention, i.e., 1-hydroxy-9-N,N-diacylamino-hexahydro-6H-dibenzo[b,d]pyrans, can be prepared by selectively protecting the phenolic 1-hydroxy group of a 9-acylamino derivative, and then further acylating the 9-amido nitrogen atom. Suitable hydroxy protecting groups include benzyl and lower alkyl groups. Such groups are readily removed when desired by reaction with sodium thioethylate in a solvent such as dimethylformamide. For example, dl-cis-1-hydroxy-3-n-pentyl-9-acetamido-6a,7,8,9,10,10a-hexahydro-6H-dibenzo[b,d]pyran can be benzylated at the 1-hydroxy group by reaction with one equivalent of benzyl chloride. The resulting benzyl ether can be acylated at the 9-amido group under forcing conditions, for instance by reaction with propionyl bromide and a strong base such as sodium hydride. The resulting diacylated derivative can be de-benzylated by hydrogenation or by reaction with sodium thioethylate to provide dl-cis-1-hydroxy-3-n-pentyl-9-(N-propionyl)acetamido-6a,7,8,9,10,10a-hexahydro-6H-dibenzo[b,d]pyran.

An alternative process for preparing amides of this invention comprises acylation of an oxime, i.e., a 9-hydroxyimino-hexahydro-dibenzo[b,d]pyran, according to the process described by Boar et al., *J. Chem. Soc.*, Perkin I, 1237 (1975). According to such process, an oxime such as 1-hydroxy-3-isohexyl-9-hydroxyimino-6a,7,8,9,10,10a-hexahydro-6H-dibenzo[b,d]pyran is reacted with any of a number of commonly utilized acylating agents, for example $C_1$–$C_7$ alkanoyl halides or phenyl-$C_1$–$C_2$ alkanoyl halides, to provide an acylated oxime, specifically a 1-hydroxy-3-isohexyl-9-acyloxyimino-6a,7,8,9,10,10a-hexahydro-6H-dibenzo[b,d]pyran. Further acylation of such a 9-acyloxyimino derivative provides a triacylated tetrahydro-dibenzopyran, which appears to be predominantly the $\Delta^8$ isomer, namely a 1-acyloxy-3-substituted-9-diacylamino-6a,7,10,10a-tetrahydro-6H-dibenzo[b,d]pyran. Mild hydrolysis of such a triacylated derivative effects removal of the 1-acyl group and one of the acyl groups at the 9-amino position to provide a 9-acylamino-tetrahydro-dibenzopyran of this invention.

The 9-alkylamino-dibenzopyrans of this invention can be acylated in a manner similar to the acylation of the primary 9-amino derivatives to afford the corresponding 9-N-alkylacylamino-hexahydro-dibenzopyrans. For example, a compound such as dl-cis-1-hydroxy-3-n-pentyl-9-allylamino-6a,7,8,9,10,10a-hexahydro-6H-dibenzo[b,d]pyran can be reacted with an acylating agent such as acetyl bromide to provide with corresponding 9-N-alkyl-acylamino derivative, namely dl-cis-1-hydroxy-3-n-pentyl-9-N-allylacetamido-6a,7,8,9,10,10a-hexahydro-6H-dibenzo[b,d]pyran.

In an analogous fashion, the 9-dialkylaminodibenzopyrans of the invention can be utilized as intermediates in the preparation of the preferred 9-acylamino derivatives of the invention. For example, a dialkylated derivative such as cis-1-hydroxy-3-(2-heptenyl)-9-N-methylisopropylamino-6a,7,8,9,10,10a-hexahydro-6H-dibenzo[b,d]pyran can be demethylated, for instance by reaction with an alkyl haloformate to form a carbonate, followed by alkaline hydrolysis, and then acylated by normal acylation conditions to provide the corresponding 9-N-isopropylacylamino-hexahydro-dibenzopyran of the invention.

The primary and secondary amines of this invention can alternatively be converted directly to an amide derivative by reaction with a carboxylic acid in the presence of a suitable coupling reagent such as N,N-dicyclohexylcarbodiimide (DCC), carbonyl-diimidazole, N-ethoxycarbonyl-2-ethoxy-1,2-dihydroquinoline (EEDQ), and the like. Reaction of a primary amine such as d-cis1-hydroxy-3-isohexyl-9-amino-6a,7,8,9,10,10a-hexahydro-6H-dibenzo[b,d]pyran with a carboxylic acid such as phenylacetic acid in the presence of DCC effects condensation to provide the corresponding 9-phenylacetamide derivative. The product is readily isolated by simply filtering the reaction mixture and removing the solvent from the filtrate.

With any of the aforementioned acylation reactions, it should be recognized that acylation may additionally be effected at the 1-hydroxy group of the dibenzopyran, thereby affording varying quantities of a 1-acyloxy-9-acylaminodibenzo[b,d]pyran, depending upon the excess of acylating agent utilized, reaction temperature, the length of reaction and the like. If desired, any such 1,9-diacylated derivative can be separated from the 9-acylamino derivative by methods such as chromatography, or alternatively, the 1,9-diacylated derivative can be treated with a mild base such as sodium bicarbonate to effect complete hydrolysis of the 1-acyloxy group, thus providing exclusively the 9-acylaminodibenzo[b,d]pyran. As previously pointed out, protection of the 1-hydroxy group prior to chemical modification obviates undesired side reactions at that site.

As noted hereinbefore, the 9-amino and 9-acylamino-hexahydro-dibenzo[b,d]pyrans provided by this invention can be alkylated by normal alkylation reactions to provide 9-alkylamino and 9-N-alkylacylamino-hexahydro-dibenzo[b,d]pyrans respectively. The alkylamino derivatives can be further alkylated to provide 9-dialkylamino derivatives. An alternative method for preparing 9-alkylamino and 9-dialkylamino-hexahydro-dibenzo[b,d]pyrans encompasses reduction of a 9-acylamino or 9-diacylamino-hexahydro-dibenzo[b,d]pyran.

For example, reaction of an acylamino compound such as 1-hydroxy-3-n-pentyl-6,6-dimethyl-9-benzoylamino-6a,7,8,9,10,10a-hexahydro-6H-dibenzo[b,d]pyran with a reducing agent such as diborane or lithium aluminum hydride effects reduction of the amide to the corresponding N-alkyl amine; in the example, the 9-benzylamino derivative. Such reductions normally are carried out in a solvent such as diethyl ether or tetrahydrofuran, and at a temperature of about 0° to 80° C. Isolation and purification of the product is accomplished by standard procedures. The 9-alkylamino-dibenzopyrans thus formed can be acylated or further alkylated in normal fashion. For example, reaction of a compound such as 1-hydroxy-3-(2-hexenyl)-9-butylamino-6a,7,8,9,10,10a-hexahydro-6H-dibenzo[b,d]pyran with phenylacetyl bromide in the presence of triethylamine effects acylation of the amino group to provide 1-hydroxy-3-(2-hexenyl)-9-(N-phenylacetyl)butylamino-6a,7,8,9,10,10a-hexahydro-6H-dibenzo[b,d]pyran.

As can readily be seen by those skilled in the art, the compounds of this invention which are fully saturated in the C-ring and which have no exocyclic double bonds, that is compounds having the above formula wherein Z is

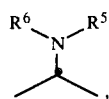

can exist as epimers. For example when an oxime of this invention is exhaustively reduced to provide a 9-amino-hexahydro-dibenzo[b,d]pyran, such compound typically is a mixture of the 9α-amino and the 9β-amino derivatives. Separation of the epimeric mixture can be accomplished if desired by fractional crystallization, column chromatography, gas liquid chromatography, high pressure liquid chromatography, and related methods. Generally, any separation of isomers is not attempted until a final product is obtained. For example, if it is desired to prepare an optically active amide such as d or l-trans-1-hydroxy-3-(1,1-dimethylheptyl)-6,6-dimethyl-9α or 9β-acetamido-6a,7,8,9,10,10a-hexahydro-6H-dibenzo[b,d]pyran, it is preferred to first prepare an oxime of the corresponding optically active d or l-trans-1-hydroxy-3-(1,1-dimethylheptyl)-6,6-dimethyl-6a,7,8,9,10,10a-hexahydro-6H-dibenzo[b,d]pyran-9-one. The oxime next is exhaustively reduced to provide an epimeric mixture of d or l-trans-1-hydroxy-3-(1,1-dimethylheptyl)-6,6-dimethyl-9-amino-6a,7,8,9,10,10a-hexahydro-6H-dibenzo[b,d]pyran. The epimeric amines are then acylated, for example by reaction with acetic anhydride, to provide an epimeric mixture of the corresponding acetamides. Separation of the acetamides thus formed provides optically active d or l-trans-1-hydroxy-3-(1,1-dimethylheptyl)-6,6-dimethyl-9α(and 9β)-acetamido-6a,7,8,9,10,10a-hexahydro-6H-dibenzo[b,d]pyran. Such optically active compounds preferably are named utilizing the currently accepted rules of nomenclature regarding absolute stereochemical configuration and thus incorporating the R and S teminology as suggested by Fletcher et al., in *Nomenclature of Organic Compounds*, Advances In Chemistry Series, 126, American Chemical Society, 1974. Accordingly, a typical optically active compound of this invention whould be named 6aR,9R,10aR-6a,10a-trans-1-hydroxy-3-(1,1-dimethylheptyl)-6,6-dimethyl-9-acetamido-6a,7,8,9,10,-10a-hexahydro-6H-dibenzo[b,d]pyran. For simplicity, the compounds named hereinafter will not utilize such nomenclature, but it should be realized that the invention comprehends such optically active isomers and racemic mixtures.

The following list presents various compounds which are illustrative of the scope of this invention.

1-hydroxy-3-n-pentyl-6,6-dimethyl-9-hydroxyimino-6a,7,8,9,10,10a-hexahydro-6H-dibenzo[b,d]pyran;

1-formyloxy-3-n-heptyl-9-methoxyimino-6a,7,8,9,10,-10a-hexahydro-6H-dibenzo[b,d]pyran;

1-isobutyryloxy-3-(1-methyl-1-hexenyl)-6,6-dimethyl-9-n-butoxyimino-6a,7,8,9,10,10a-hexahydro-6H-dibenzo[b,d]pyran;

1-hydroxy-3-(2-decenyl)-9-hydroxyamino-6a,7,8,9,10,10a-hexahydro-6H-dibenzo[b,d]pyran;

1-hydroxy-3-(1,2-dimethyloctyl)-9-methoxyamino-6a,7,8,9,10,10a-hexahydro-6H-dibenzo[b,d]pyran;

1-hydroxy-3-(1,2,3-trimethylheptyl)-6,6-dimethyl-9-amino-6a,7,8,9,10,10a-hexahydro-6H-dibenzo[b,d]pyran;

dl-cis-1-hydroxy-3-n-hexyl-3,3-dimethyl-9-acetamido-6a,7,8,9,10,10a-hexahydro-6H-dibenzo[b,d]pyran;

d-cis-1-acetoxy-3-(1-ethylpentyl)-6,6-dimethyl-9-(N,N-dipropionylamino)-6a,7,8,9,10,10a-hexahydro-6H-dibenzo[b,d]pyran;

1-trans-1-hydroxy-3-(1,2-dimethylheptyl)-9-N-ethylamino-6a,7,8,10a-tetrahydro-6H-dibenzo[b,d]pyran;

1-hydroxy-3-n-pentyl-6,6-dimethyl-9-hexanoyloxyamino-6a,7,8,9,10,10a-hexahydro-6H-dibenzo[b,d]pyran;

1-hydroxy-3-n-octyl-9-acetoxyethylamino-6a,7,8,9,10,10a-hexahydro-6H-dibenzo[b,d]pyran;

1-acetoxy-3-n-heptyl-9-(N-isobutyl)-hexanamido-6a,7,8,10a-tetrahydro-6H-dibenzo[b,d]pyran;

1-hydroxy-3-(1,2-dimethyl-1-hexenyl)-6,6-dimethyl-9-N,N-diisopropylamino-6a,7,8,9,10,10a-hexahydro-6H-dibenzo[b,d]pyran;

dl-cis-1-hydroxy-3-(1,1-dimethylpentyl)-6,6-dimethyl-9-(2-propenyl)amino-6a,7,8,9,10,10a-hexahydro-6H-dibenzo[b,d]pyran;

dl-trans-1-hydroxy-3-(1,2-dimethylheptyl)-6,6-dimethyl-9-α-acetamido-6a,7,8,9,10,10a-hexahydro-6H-dibenzo[b,d]pyran;

d-trans-1-hydroxy-3-(1,2-dimethyl-1-heptenyl)-6,6-dimethyl-9-β-acetamido-6a,7,8,9,10,10a-hexahydro-6H-dibenzo[b,d]pyran;

1-trans-1-hydroxy-3-(1,1-dimethyl-2-heptenyl)-6,6-dimethyl-9-α-butyramido-6a,7,8,9,10,10a-hexahydro-6H-dibenzo[b,d]pyran;

1-hydroxy-3-n-octyl-9-isoheptanamido-6a,7,10,10a-tetrahydro-6H-dibenzo[b,d]pyran;

dl-cis-1-propionoxy-3-n-hexyl-6,6-dimethyl-9-(N-isobutyl) propionamido-6a,7,8,10a-tetrahydro-6H-dibenzo[b,d]pyran;

1-hydroxy-3-n-hexyl-6,6-dimethyl-9-N-benzylamino-6a,7,8,10a-tetrahydro-6H-dibenzo[b,d]pyran hydrobromide;

dl-cis-1-hydroxy-3-(1,2-dimethylheptyl)-6,6-dimethyl-9-methylamino-6a,7,8,9,10,10a-hexahydro-6H-dibenzo[b,d]pyran acetic acid salt;

dl-cis-1-acetoxy-3-n-pentyl-9-(N-isobutyl-N-phenylethyl)amino-6a,7,8,9,10,10a-hexahydro-6H-dibenzo[b,d]pyran;

d-trans-1-hydroxy-3-(3-octenyl)-9-(N-benzyl-N-phenylethyl)amino-6a,7,8,9,10,10a-hexahydro-6H-dibenzo[b,d]pyran succinic acid salt;

1-hydroxy-3-isodecyl-6,6-dimethyl-9-(N-3-butenyl)ethylamino-6a,7,8,9,10,10a-hexahydro-6H-dibenzo[b,d]pyran;

1-hydroxy-3-(1,2-dimethylhexyl)-9-(N,N-dimethyl-N-allyl)ammonium-6a,7,8,9,10,10a-hexahydro-6H-dibenzo[b,d]pyran bromide;

1-hydroxy-3-n-octyl-9-(N-benzoylhexanoylamino-6a,7,10,10a-tetrahydro-6H-dibenzo[b,d]pyran;

dl-trans-1-hydroxy-3-(1-ethylbutyl)-6,6-dimethyl-9-(N-ethyl)heptanoylamino-6a,7,8,9,10,10a-hexahydro-6H-dibenzo[b,d]pyran;

dl-cis-1-hydroxy-3-(1,1-dimethylheptyl)-6,6-dimethyl-9-(N-3-butynyl)amino-6a,7,8,9,10,10a-hexahydro-6H-dibenzo[b,d]pyran hydrochloride.

The 9-amino-dibenzo[b,d]pyran derivativies of this invention defined by the above general formula are new chemical compounds having useful pharmacological activity, and many additionally are useful as intermediates in the synthesis of pharmacologically active compounds. An additional aspect of this invention therefore are pharmaceutical formulations containing at least one biologically active compound of this invention in association with one or more suitable diluents, carriers or excipients therefor. Additionally, other pharmacologically active drugs can be incorporated into the formulation containing an active ingredient of this invention. A particularly preferred pharmaceutical formulation according to this invention is one useful in the treatment of hypertension. Especially preferred formulations are those containing as active ingredient a 9-amido derivative of this invention.

The formulations contemplated by this invention take a form which is readily conducive to the particular route of administration desired in each particular case. For oral administration, a compound of this invention is admixed with carriers and diluents such as dextrose, lactose, mannitol, cocoa butter, ethyl lactate, methyl cellulose, calcium silicate, potato starch, microcrystalline cellulose, polyvinylpyrrolidone, potassium benzoate, and related excipients. Such formulations can be molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water.

A particularly preferred formulation useful for treating hypertension in human subjects comprises a compound such as dl-trans-1-hydroxy-3-(1,1-dimethylheptyl)-6,6-dimethyl-9-acetamido-6a,7,8,9,10,10a-hexahydro-6H-dibenzo[b,d]pyran in the amount of about 0.01 mg. to about 1.0 mg. in combination with a carrier such as sucrose or starch in the amount of about 500 mg. Such formulation can be molded into tablets which can be administered to a subject suffering from high blood pressure at the rate of about 1 to about 4 tablets per day.

As already pointed out, the compounds of this invention have a variety of utilities. Representative compounds of this invention have demonstrated activity in one or more standard tests designed to show analgesic, anti-glaucoma, anti-depressant and anti-anxiety activity, as well as hypotensive activity. The most potent compounds provided herein appear to be the 9-amido derivatives (e.g. $R^6$ and $R^7$ in the above formulae are alkanoyl), even though other compounds of the invention are useful pharmacologically. For example, dl-trans-1-hydroxy-3-(1,1-dimethylheptyl)-6,6-dimethyl-9-hydroxyimino-6a,7,8,9,10,10a-hexahydro-6H-dibenzo[b,d]pyran demonstrated an $ED_{50}$ of 2 mg./kg. in analgesic activity when tested subcutaneously in the mouse writhing assay. Similarly, dl-trans-1-hydroxy-3-(1,1-dimethylheptyl)-6,6-dimethyl-9-hydroxyamino-6a,7,8,9,10,10a-hexahydro-6H-dibenzo[b,d]pyran caused a response in the mouse activity assay at a minimum effective dose (MED) of only 5.0 mg./kg. Moreover, when tested in the septal lesion rat assay, dl-trans-1-hydroxy-3-(1,1-dimethylheptyl)-6,6-dimethyl-9-(N-ethyl)acetamido-6a,7,8,9,10,10a-hexahydro-6H-dibenzo[b,d]pyran demonstrated an MED of 10.0 mg./kg. When tested in the dog for its ability to reduce blood pressure, dl-trans-1-hydroxy-3-(1,1-dimethylheptyl)-6,6-dimethyl -9-acetamido-6a,7,8,9,10,10a-hexahydro-6H-dibenzo[b,d]pyran demonstrated an intravenous MED of one-half microgram/kg.

As can readily be seen from the above discussion regarding biological activity, many of the compounds of this invention are useful in the treatment of hypertension, anxiety, depression, pain, glaucoma and related maladies. The compounds can thus be used to treat animals and humans alike suffering from such conditions. A further embodiment of this invention therefore is a method of treating hypertension in mammals comprising administering an effective dose for treating hypertension of a hypotensively active compound of this invention to a subject suffering from hypertension and in need of treatment or to a subject suspected of developing hypertension and in need of prophylactic treatment. An especially preferred method of treating hypertension according to this invention comprises administering a compound of this invention having an amido moiety at the 9-position (i.e. $R^5$ is $C_1$–$C_7$ alkanoyl).

The hypotensively active compounds of this invention can be administered by any of a number of routes, including the oral, subcutaneous, intramuscular and intravenous routes. Typical dosages useful for the treatment of humans will of course vary depending upon the particular condition being treated and the size and of the patient, but typically will range from about 0.001 to about 20 mg. total daily dose per patient. Preferred daily dosages commonly utilized when treating hypertension, for example, will range from about 0.1 to about 10 mg. per subject. A typical treatment of hypertension will include, for example, the administration to a subject of about 5 mg. per day of dl-1-hydroxy-3-(1,2-dimethylheptyl)-9-(2,6-dioxopiperidino)-6a,7,8,9,10,10a-hexahydro-6H-dibenzo[b,d]pyran. A preferred treatment comprises administering about 2 mg. per day of dl-trans-1-hydroxy-3-(1,1-dimethylheptyl)-6,6-dimethyl-9-acetamido-6a,7,8,9,10,10a-hexahydro-6H-dibenzo[b,d]pyran.

The preparation of the 9-amino-dibenzopyran compounds comprehended by this invention is more fully described in the following examples. It is of course to be understood, however, that the examples are illustrative of the compounds embraced by the invention and of the methods commonly employed in their preparation and are not to be construed as limiting the invention to any of the particular compounds or methods specifically described.

EXAMPLE 1 dl-trans-1-Hydroxy-3-(1,1-dimethylheptyl)-6,6-dimethyl-9-hydroxyimino-6a,7,8,9,10,10a-hexahydro-6H-dibenzo[b,d]pyran A solution of 4.0 g. of dl-trans-1-hydroxy-3-(1,1-dimethylheptyl)-6,6-dimethyl-6a,7,8,9,10,10a-hexahydro-6H-dibenzo[b,d]pyran-9-one and 1.155 g. of hydroxylamine hydrochloride dissolved in 60 ml. of ethanol and 10 ml. of water was stirred while 4.4 ml. of 5 N sodium hydroxide was added in one portion. The reaction mixture then was heated to reflux and stirred at that temperature for thirty minutes. After cooling the reaction mixture to room temperature, it was added to 100 g. of ice and then acidified to pH 2.5 by the addition of concentrated hydrochloric acid. The aqueous acidic reaction mixture then was extracted several times with diethyl ether. The ethereal extracts were combined, washed with five percent aqueous sodium bicarbonate solution and with water, and dried. Removal of the solvent by evaporation under reduced pressure afforded 2.0 g. of the product as an oil. The oil was crystallized from 50 ml. of n-hexane to provide 3.8 g. of dl-trans-1-hydroxy-3-(1,1-dimethylheptyl)-6,6-dimethyl-9-hydroxyimino-6a,7,8,9,10,10a-hexahydro-6H-dibenzo[b,d]pyran as a white powder. M.P. 143°–145° C.

Analysis calc. for $C_{24}H_{37}NO_3$: Theory: C, 74.38; H, 9.62; N, 3.61. Found: C, 74.61; H, 9.37; N, 3.78.

m/e: calc. 387; found 387.

The above procedure was repeated utilizing 7.5 g. of optically active (−)-trans-1-hydroxy-3-(1,1-dimethylheptyl)-6,6-dimethyl-6a,7,8,9,10,10a-hexahydro-6H-dibenzo[b,d]pyran-9-one as the starting ketone. Isolation of the product was carried out as described above and provided 5 g. of an oil. m/e: calc. 387; found 387. $[\alpha]_D^{CHCl_3} = +4.0$ $[\alpha]_{365}^{CHCl_3} = +34.6$.

Chromatographic purification of a sample of such product, utilizing a high pressure liquid chromatographic procedure, effected separation of the syn and anti isomers of the optically active oxime.

syn-trans-1-hydroxy-3-(1,1-dimethylheptyl)-6,6-dimethyl-9-hydroxyimino-6a,7,8,9,10,10a-hexahydro-6H-dibenzo[b,d]pyran;
$[\alpha]_D^{CHCl_3} = +34.8°$
$[\alpha]_{365}^{CHCl_3} = +137.3°$ anti-trans-1-hydroxy-3-(1,1-dimethylheptyl)-6,6-dimethyl-9-hydroxyimino-6a,7,8,9,10,10a-hexahydro-6H-dibenzo[b,d]pyran;
$[\alpha]_D^{CHCl_3} = -26.8°$
$[\alpha]_{365}^{CHCl} = -71.9°$

EXAMPLE 2 dl-trans-1-Hydroxy-3-(1,1-dimethylheptyl)-6,6-dimethyl-9-hydroxyamino-6a,7,8,9,10,10a-hexahydro-6H-dibenzo[b,d]pyran To a stirred solution of 3.87 g. of dl-trans-1-hydroxy-3-(1,1-dimethylheptyl)-6,6-dimethyl-9-hydroxyimino-6a,7,8,10,10a-hexahydro-6H-dibenzo[b,d]pyran (prepared as described in Example 1) dissolved in 50 ml. of methanol containing a trace of bromocresol green was added 1.0 g. of sodium cyanoborohydride in one portion. The reaction mixture was stirred at 24° C. while concentrated methanolic hydrogen chloride was added portionwise until the color of the solution turned yellow. The acidic reaction mixture then was stirred for two hours at 24° C., after which time the solvent was removed by evaporation under reduced pressure to provide an oil. The oil was suspended in 50 ml. of five percent aqueous sodium bicarbonate, and then extracted into diethyl ether. The ethereal extracts were combined, washed with water and dried. Removal of the solvent afforded 3.72 g. of a white foam, dl-trans-1-hydroxy-3-(1,1-dimethylheptyl)-6,6-dimethyl-9-hydroxyamino-6a,7,8,9,10,10a-hexahydro-6H-dibenzo[b,d]pyran.

Analysis Calc. for $C_{24}H_{39}NO_3$: Theory, C, 73.99; H, 10.09; N, 3.60. Found: C, 73.69; H, 9.85; N, 3.39.

m/e: calc. 389; found 389.

The white foam was reacted with 1.16 g. of maleic acid in diethyl ether to provide crystalline dl-trans-1-hydroxy-3-(1,1-dimethylheptyl)-6,6-dimethyl-9-hydroxyamino-6a,7,8,9,10,10a-hexahydro-6H-dibenzo[b,d]pyran maleate salt. M.P. 145°–147° C.

Analysis calc. for $C_{28}H_{43}NO_7$: Theory: C, 66.51; H, 8.57; N, 2.77. Found: C, 66.34; H, 8.36; N, 3.04.

EXAMPLE 3 dl-trans-1-Hydroxy-3-(1,1-dimethylheptyl)-6,6-dimethyl-9-amino-6a,7,8,9,10,10a-hexahydro-6H-dibenzo[b,d]pyran A solution of 1.93 g. of dl-trans-1-hydroxy-3-(1,1-dimethylheptyl)-6,6-dimethyl-9-hydroxyimino-6a,7,8,9,10,10a-hexahydro-6H-dibenzo[b,d]pyran (from Example 2) in 100 ml. of methanol and 25 ml. of liquid anhydrous ammonia containing 1.0 g. of Raney nickel was stirred and heated at 100° C. for six hours under a hydrogen gas atmosphere at 1000 psi. The reaction mixture then was cooled to room temperature and filtered. The filtrate was concentrated by evaporation of the solvent under reduced pressure to provide a solid mass. The solid was dissolved in 300 ml. of diethyl ether and washed with 50 ml. of 1 N hydrochloric acid, 50 ml. of five percent aqueous sodium bicarbonate, and with water. The ethereal solution was dried and concentrated to dryness by evaporation under reduced pressure to afford 500 mg. of a white solid. The solid so formed was recrystallized from diethyl ether and hexane to provide 1.85 g. of dl-trans-1-hydroxy-3-(1,1-dimethylheptyl)-6,6-dimethyl-9-amino-6a,7,8,9,10,10a-hexahydro-6H-dibenzo[b,d]pyran.

Analysis calc. for $C_{24}H_{39}NO_2$: Theory: C, 77.16; H, 10.52; N, 3.75. Found: C, 77.77; H, 10.08; N, 3.27.

m/e: calc. 373; found 373.

EXAMPLE 4 dl-trans-1-hydroxy-3-(1,1-dimethylheptyl)-6,6-dimethyl-9-amino-6a,7,8,9,10,10a-hexahydro-6H-dibenzo[b,d]pyran hydrogen maleate A solution of 340 mg. of dl-trans-1-hydroxy-3-(1,1-dimethylheptyl)-6,6-dimethyl-9-amino-6a,7,8,9,10,10a-hexahydro-6H-dibenzo[b,d]pyran in 50 ml. of diethyl ether containing 164 mg. of maleic acid was stirred and heated at reflux for ten minutes. The product precipitated out of solution and was collected by filtration to provide dl-trans-1-hydroxy-3-(1,1-dimethylheptyl)-6,6-dimethyl-9-amino-6a,7,8,9,10,10a-hexahydro-6H-dibenzo[b,d]pyran as a white solid.

Analysis calc. for $C_{28}H_{43}NO_6$: Theory: C, 68.68; H, 8.85; N, 2.86. Found: C, 68.51; H, 8.57; N, 2.66.

EXAMPLE 5 dl-trans-1-Hydroxy-3-(1,1-dimethylheptyl)-6,6-dimethyl-9-acetamido-6a,7,8,9,10,10a-hexahydro-6H-dibenzo[b,d]pyran To a stirred solution of 750 mg. of dl-trans-1-hydroxy-3-(1,1-dimethylheptyl)-6,6-dimethyl-9-amino-6a,7,8,9,10,10a-hexahydro-6H-dibenzo[b,d]pyran in 10 ml. of methanol was added in one portion 1.5 ml. of triethylamine and 1.0 ml. of acetic anhydride. The reaction mixture was stirred for twelve hours at 24° C., and then added to 50 ml. of water. The aqueous reaction mixture then was extracted with diethyl ether. The ethereal extracts were combined, washed with water and with ten percent aqueous sodium bicarbonate solution, and dried. Removal of the solvent by evaporation under reduced pressure afforded 840 mg. of a solid foam. The foam was then applied to a column packed with 30 g. of Woelm Acitivity I Silica gel, and eluted with ethyl acetate. Fractions shown by thin layer chromatography to contain the desired product were combined and concentrated to dryness to provide 735 mg. of dl-trans-1-hydroxy-3-(1,1-dimethylheptyl)-6,6-dimethyl-9-acetamido-6a,7,8,9,10,10a-hexahydro-6H-dibenzo[b,d]pyran.

Analysis calc. for $C_{26}H_{41}NO_3$: Theory: C, 75.14; H, 9.94; N, 3.37. Found: C, 75.51; H, 9.75; N, 3.43.
m/e: 415; calc. 415.

EXAMPLE 6

Following the procedure set forth in Example 5, 5.98 g. of dl-trans-1-hydroxy-3-(1,1-dimethylheptyl)-6,6-dimethyl-9-amino-6a,7,8,9,10,10a-hexahydro-6H-dibenzo[b,d]pyran was reacted with 8.0 ml. of acetic anhydride and 12 ml. of triethylamine in 100 ml. of methanol. Normal workup provided 3.97 g. of the product as a white solid. The product was chromatographed over a column packed with 240 g. of Woelm Activity No 1. Silica gel. The appropriate fractions were carefully collected and the solvent was removed therefrom to provide 1.06 g. of dl-trans-1-hydroxy-3-(1,1-dimethylheptyl)-6,6-dimethyl-9α-acetamido-6a,7,8,9,10,10a-hexahydro-6H-dibenzo[b,d]pyran. A sample of this axial isomer was crystallized from 20 ml. of n-hexane. M.P. 195°–197° C.

Analysis calc. for $C_{26}H_{41}NO_3$: Theory: C, 75.14; H, 9.94; N, 3.37. Found: C, 75.37; H, 10.05; N, 3.12.

Further chromatography and collection of the appropriate fractions provided, after evaporation of the solvent, 2.16 g. of dl-trans-1-hydroxy-3-(1,1-dimethylheptyl)-6,6-dimethyl-9β-acetamido-6a,7,8,9,10,10a-hexahydro-6H-dibenzo[b,d]pyran. M.P. 200°–202° C.

Analysis calc. for $C_{20}H_{41}NO_3$: Theory: C, 75.14; H, 9.94; N, 3.37. Found: C, 74.95; H, 9.58; N, 3.31.

EXAMPLE 7 dl-trans-1-Hydroxy-3-(1,1-dimethylheptyl)-6,6-dimethyl-9-propionamido-6a,7,8,9,10,10a-hexahydro-6H-dibenzo[b,d]pyran A solution of 373 g. of dl-trans-1-hydroxy-3-(1,1-dimethylheptyl)-6,6-dimethyl-9-amino-6a,7,8,9,10,10a-hexahydro-6H-dibenzo[b,d]pyran in 20 ml. of methanol containing 1.3 g. of propionic anhydride and 2.5 ml. of triethylamine was stirred at ambient temperature for forty-eight hours. The reaction mixture then was diluted with 25 ml. of water, and the aqueous mixture was stirred for two hours at room temperature. The excess methanol then was removed by evaporation under reduced pressure and the product was extracted from the aqueous mixture into diethyl ether. The ethereal extracts were combined, washed with water, 2 N hydrochloric acid, 10 percent aqueous sodium bicarbonate, and dried. Removal of the solvent by evaporation under reduced pressure afforded a foam which next was further purified by chromatography over 20 g. of silica gel, eluting with diethyl ether. Fractions of 10 ml. volume were collected, and fractions 5 through 30 were combined and the solvent evaporated therefrom to provide 434 mg. of dl-trans-1-hydroxy-3-(1,1-dimethylheptyl)-6,6-dimethyl-9-propionamido-6a,7,8,9,10,10a-hexahydro-6H-dibenzo[b,d]pyran.

Analysis calc. for $C_{27}H_{43}NO_3$: Theory: C, 75.48; H, 10.09; N, 3.26. Found: C, 75.23; H, 9.84; N, 3.26.
m/e: calc. 429; found 429.

EXAMPLE 8 dl-trans-1-Acetoxy-3-(1,1-dimethylheptyl)-6,6-dimethyl-9-acetamido-6a,7,8,9,10,10a-hexahydro-6H-dibenzo[b,d]pyran A solution containing 373 mg. of dl-trans-1-hydroxy-3-(1,1-dimethylheptyl)-6,6-dimethyl-9-amino-6a,7,8,9,10,10a-hexahydro-6H-dibenzo[b,d]pyran, 10 ml. of acetic anhydride and 10 ml. of pyridine was stirred at room temperature for forty-eight hours. The reaction mixture was cooled and the methanol was removed by evaporation. The residue was dissolved in diethyl ether, washed with water, 1 N hydrochloric acid, and brine. The ethereal solution was dried and the solvent was removed by evaporation to provide the product as a white foam. The foam so produced was purified by chromatography over a column packed with 20 g. of Woelm Activity No. 1 silica gel, eluting with diethyl ether. Evaporation of the solvent from the appropriate fractions afforded 420 mg. of dl-trans-1-acetoxy-3-(1,1-dimethylheptyl)-6,6-dimethyl-9-acetamido-6a,7,8,9,10,10a-hexahydro-6H-dibenzo[b,d]pyran.

Analysis calc. for $C_{28}H_{43}NO_4$: Theory: C, 73.49; H, 9.47; N, 3.06. Found: C, 73.26; H, 9.36; N, 3.28.
m/e: calc. 457; found 457.

EXAMPLE 9 dl-trans-1-Hydroxy-3-(1,1-dimethylheptyl)-6,6-dimethyl-9-formamido-6a,7,8,9,10,10a-hexahydro-6H-dibenzo[b,d]pyran A solution of 15 ml. of acetic anhydride and 7.5 ml. of 98 percent formic acid was stirred and heated at reflux for fifteen minutes. The mixture was cooled to room temperature, and then 2.5 g. of sodium acetate and 373 mg. of dl-trans-1-hydroxy-3-(1,1-dimethylheptyl)-6,6-dimethyl-9-amino-6a,7,8,9,10,10a-hexahydro-6H-dibenzo[b,d]pyran were added to it. The reaction mixture was stirred for four hours at room temperature, and then added to a solution of methanol containing sodium carbonate and water. The mixture was stirred for one hour, after which time the solvent was removed by evaporation under reduced pressure. The aqueous layer was extracted with diethyl ether, and the ethereal extracts were combined, washed with water and dried. Removal of the solvent by evaporation afforded 410 mg. of the product as a white solid. The solid so formed was purified by chromatography over 20 g. of silica gel to provide 276 mg. of dl-trans-1-hydroxy-3-(1,1-dimethylheptyl)-6,6-dimethyl-9-formamido-6a,7,8,9,10,10a-hexahydro-6H-dibenzo[b,d]pyran.

Analysis calc. for $C_{25}H_{39}NO_3$: Theory: C, 74.77; H, 9.79; N, 3.49. Found: C, 74.61; H, 9.53; N, 3.64.
m/e: calc. 401; found 401.

EXAMPLE 10 dl-trans-1-acetoxy-3-(1,1-dimethylheptyl)-6,6-dimethyl-9-(N,N-diacetylamino)-6a,7,10,10a-tetrahydro-6H-dibenzo[b,d]pyran A solution of 2.59 g. of dl-trans-1-hydroxy-3-(1,1-dimethylheptyl)-6,6-dimethyl-9-hydroxyimino- 6a,7,8,9,10,10a-hexahydro-6H-dibenzo[b,d]pyran in 25 ml. of acetic anhydride and 75 ml. of pyridine was stirred under a nitrogen gas atmosphere and heated to reflux for twenty-four hours. After cooling the reaction mixture to room temperature, the solvent was removed therefrom by evaporation under reduced pressure to provide an oily residue. The residue was dissolved in 50 ml. of diethylether and 50 ml. of water and stirred for one hour. The mixture was filtered and the organic layer was separated. The ethereal solution was washed with 1 N hydrochloric acid, water, saturated sodium chloride solution and dried. Removal of the solvent afforded 3.57 g. of a dark oil which was then chromatographed over 100 g. of Woelm Activity I silica gel, eluting with fifty percent hexane-diethyl ether. The fractions containing the major product were combined and concentrated to dryness to provide 3.12 g. of predominantly dl-1-acetoxy-3-(1,1-dimethylheptyl)-6,6-dimethyl-9-(N,N-diacetylamino)-6a,7,10,10a-tetrahydro-6H-dibenzo[b,d]pyran, with a minor quantity of the $\Delta^9$ compound.

m/e: calc. 497; found 497.

EXAMPLE 11 dl-trans-1-Hydroxy-3-(1,1-dimethylheptyl)-6,6-dimethyl-9-(acetamido)-6a,7,10,10a-tetrahydro-6H-dibenzo[b,d]pyran A solution of 5.4 g. of dl-trans-1-acetoxy-3-(1,1-dimethylheptyl)-6,6-dimethyl-9-(N,N-diacetylamino)-6a,7,10,10a-tetrahydro-6H-dibenzo[b,d]pyran in 150 ml. of methanol containing 50 ml. of twenty percent aqueous potassium carbonate. The reaction mixture was stirred at 24° C. for two hours, and then concentrated to dryness by evaporation under reduced pressure. The oil thus formed was suspended in 100 ml. of water, and the aqueous mixture was extracted with diethyl ether. The ethereal extracts were combined, diluted with 20 ml. of ethyl acetate, and then washed with 2H hydrochloric acid, ten percent aqueous sodium bicarbonate, and dried. Removal of the solvent afforded 1.54 g. of a solid which was then crystallized from hexane to afford 1.33 g. of dl-trans-1-hydroxy-3-(1,1-dimethylheptyl)-6,6-dimethyl-9-(acetamido)-6a,7,10,10a-tetrahydro-6H-dibenzo[b,d]pyran. M.P. 186°–188° C.

Analysis calc. for $C_{28}H_{41}NO_4$: Theory: C, 73.81; H, 9.07; N, 3.07; O, 14.05. Found: C, 73.74; H, 8.79; N, 3.16; O, 13.90.

m/e: calc. 413 found 413.

EXAMPLE 12 dl-1-Hydroxy-3-(1,1-dimethylheptyl)-6,6-dimethyl-9-(acetamido)-6a,7,8,9,10,10a-hexahydro-6H-dibenzo[b,d]pyran A solution of 1.177 g. of dl-1-hydroxy-3-(1,1-dimethylheptyl)-6,6-dimethyl-9-(acetamido)-6a,7,10,10a-tetrahydro-6H-dibenzo[b,d]pyran in 100 ml. of ten percent aqueous ethanol containing 0.5 g. of five percent palladium suspended on carbon was stirred at 50° C. for 12 hours under a hydrogen atmosphere at 50 psi. The reaction mixture then was cooled to room temperature and filtered. The filtrate was concentrated to dryness by evaporation under reduced pressure to provide 1.06 g. of dl-trans-1-hydroxy-3-(1,1-dimethylheptyl)-6,6-dimethyl-9-(acetamido)-6a,7,8,9,10,10a-hexahydro-6H-dibenzo[b,d]pyran. Nuclear magnetic resonance spectroscopy demonstrated the product thus formed to be indentical to that prepared in Example 5.

EXAMPLE 13 dl-trans-1-Hydroxy-3-(1,1-dimethylheptyl)-6,6-dimethyl-9-ethylamino-6a,7,8,9,10,10a-hexahydro-6H-dibenzo[b,d]pyran To a stirred solution of 650 mg. of dl-trans-1-hydroxy-3-(1,1-dimethylheptyl)-6,6-dimethyl-9-acetamido-6a,7,8,9,10,10a-hexahydro-6H-dibenzo[b,d]-pyran in 5 ml. of dry tetrahydrofuran was added dropwise over five minutes 5 ml. of 1 M diborane in tetrahydrofuran. The reaction mixture was heated to reflux and stirred at that temperature for five hours. The reaction mixture then was cooled to 0° C. and stirred while 5 ml. of 2 N hydrochloric acid was added to decompose any excess diborane. The aqueous acidic reaction mixture was heated to 100° C. for thirty minutes, and then again cooled to 0° C. The solution was basified with ten percent aqueous sodium bicarbonate, and the product was extracted therefrom into diethyl ether. The ethereal extracts were combined and concentrated to dryness by evaporation under reduced pressure to provide 600 mg. of dl-trans-1-hydroxy-3-(1,1-dimethylheptyl)-6,6-dimethyl-9-ethylamino-6a,7,8,9,10,10a-hexahydro-6H-dibenzo[b,d]pyran.

EXAMPLE 14 dl-trans-1-Hydroxy-3-(1,1-dimethylheptyl)-6,6-dimethyl-9-(N-ethyl)acetamido-6a,7,8,9,10,10a-hexahydro-6H-dibenzo[b,d]pyran A solution of 600 mg. of dl-trans-1-hydroxy-3-(1,1-dimethylheptyl)-6,6-dimethyl-9-ethylamino-6a,7,8,9,10,10a-hexahydro-6H-dibenzo[b,d]pyran in 25 ml. of methanol was stirred at room temperature while a mixture of 1.5 ml. of triethyl amine and 1.5 ml. of acetic anhydride was added in one portion. The reaction mixture was stirred at 25° C. for thirty-six hours. The solvent was then removed from the reaction mixture by evaporation under reduced pressure, and the resulting residue was dissolved in diethyl ether and washed with water and with aqueous sodium bicarbonate solution, and dried. The solvent was then removed by evaporation under reduced pressure, thus leaving 550 mg. of a white froth. The product so formed was chromatographed over 50 g. of Woelm Activity I silica gel, eluting with ethyl acetate. The fractions shown by thin layer chromatography to contain the major product were combined and concentrated to dryness to afford 410 mg. of dl-trans-1-hydroxy-3-(1,1-dimethylheptyl)-6,6-dimethyl-9-(N-ethyl)acetamido-6a,7,8,10,-10a-hexahydro-6H-dibenzo[b,d]pyran. m/e 443.

Analysis calc. for $C_{28}H_{45}NO_3$: Theory: C, 75.80; H, 10.22; N, 3.16; O, 10.82. Found: C, 75.56; H, 9.93; N, 2.98; O, 10.89

A minor component was shown to consist of dl-trans-1-acetoxy-3-(1,1-dimethylheptyl)-6,6-dimethyl-9-(N-ethyl)acetamido-6a,7,8,9,10,10a-hexahydro-6H-dibenzo[b,d]pyran. m/e 485.

EXAMPLE 15 dl-trans-1-hydroxy-3-(1,1-dimethylheptyl)-6,6-dimethyl-9-dimethylamino-6a,7,8,9,10,10a-hexahydro-6H-dibenzo[b,d]pyran A solution of 1.48 g. of dl-trans-1-hydroxy-3-(1,1-dimethylheptyl)-6,6-dimethyl-6a,7,8,9,10,10a-hexahydro-6H-dibenzo[b,d]pyran-9-one in 50 ml. of methanol containing 3.24 g. of dimethylamine hydrochloride, 3.03 g. of triethylamine and 378 mg. of sodium cyanoborohydride was stirred at ambient temperature for sixty hours. The reaction mixture was concentrated in volume by evaporation of the solvent, and the residue was dissolved in 50 ml. of diethyl ether. The ethereal solution was washed with 0.5 N hydrochloric acid, water, 10 percent aqueous sodium bicarbonate, and again with water. The solution was dried and the solvent then was removed by evaporation under reduced pressure to provide the product as an oil. The oil was dissolved in 50 ml. of hexane and diluted with 1.0 ml. of 6.5 N methanolic hydrochloric acid solution. The precipitated solid which formed was shown to be 1.67 g. of dl-trans-1-hydroxy-3-(1,1-dimethylheptyl)-6,6-dimethyl-9-dimethylamino-6a,7,8,9,10,10a-hexahydro-6H-dibenzo[b,d]pyran hydrochloride.

Analysis calc. for $C_{26}H_{44}NO_2Cl$: Theory: C, 71.28; H, 10.12; N, 3.20; Cl, 8.09. Found: C, 70.60; H, 9.78; N, 2.98; Cl, 7.62.

m/e: calc. 401; found 401.

EXAMPLES 16–19

Following the general procedure set out in Example 15, dl-trans-1-hydroxy-3-(1,1-dimethylheptyl)-6,6-dimethyl-6a,7,8,9,10,10a-hexahydro-6H-dibenzo[b,d]pyran-9-one was reacted with the appropriate amine to afford the following compounds:

dl-trans-1-hydroxy-3-(1,1-dimethylheptyl)-6,6-dimethyl-9-isopropylamino-6a,7,8,9,10,10a-hexahydro-6H-dibenzo[b,d]pyran hydrochloride.

Analysis calc. for $C_{27}H_{46}NO_2Cl$: Theory: C, 71.73; H, 10.26; N, 3.10; Cl, 7.84. Found: C, 71.44; H, 10.00; N, 3.28; Cl, 7.54.

m/e: calc. 415; found 415.

dl-trans-1-hydroxy-3-(1,1-dimethylheptyl)-6,6-dimethyl-9-(2-propynyl)amino-6a,7,8,9,10,10a-hexahydro-6H-dibenzo[b,d]pyran Analysis calc. for $C_{27}H_{41}NO_2$: Theory: C, 78.78; H, 10.04; N, 3.40. Found: C, 78.55; H, 9.83; N, 3.39.

m/e: calc. 411; found 411.

dl-trans-1-hydroxy-3-(1,1-dimethylheptyl)-6,6-dimethyl-9-N-methyl-N-(2-propynyl)amino-6a,7,8,9,10,10a-hexahydro-6H-dibenzo[b,d]pyran hydrochloride.

Analysis calc. for $C_{28}H_{44}NO_2Cl$: Theory: C, 72.78; H, 9.60; N, 3.03; Cl, 7.67. Found: C, 71.01; H, 9.54; N, 2.52; Cl, 7.13.

m/e: calc. 425; found 425.

dl-trans-1-hydroxy-3-(1,1-dimethylheptyl)-6,6-dimethyl-9-benzylamino-6a,7,8,9,10,10a-hexahydro-6H-dibenzo[b,d]pyran.

Analysis calc. for $C_{31}H_{45}NO_2$: Theory: C, 80.30; H, 9.78; N, 3.02. Found: C, 80.31; H, 9.86; N, 3.01.

m/e: calc. 463; found 463.

EXAMPLE 20 dl-trans-1-Hydroxy-3-(1,1-dimethylheptyl)-6,6-dimethyl-9-(2-hydroxyethyl)amino-6a,7,8,9,10,10a-hexahydro-6H-dibenzo-[b,d]pyran.

To a solution of 1.48 g. of dl-trans-1-hydroxy-3-(1,1-dimethylheptyl)-6,6-dimethyl-6a,7,8,9,10,10a-hexahydro-6H-dibenzo[b,d]pyran-9-one in 50 ml. of methanol was added in one portion 2.44 g. of ethanolamine. The reaction mixture was stirred at room temperature for thirty minutes, and then was diluted with a solution of 1.5 ml. of 6.5 N hydrochloric acid in 10 ml. of methanol. The acidic mixture was stirred for fifteen minutes, and then 378 mg. of sodium cyanoborohydride was added. The reaction mixture then was stirred for seventy-two hours at room temperature. The reaction mixture was filtered and the solvent was evaporated to provide the product as a gum. The crude product was dissolved in 100 ml. of diethyl ether and washed with 0.5 N hydrochloric acid, saturated sodium chloride, and with 10 percent sodium bicarbonate solution. The ethereal layer was dried and the solvent was evaporated therefrom to afford a white foam. The foam was dissolved in 50 ml. of hexane, to which was added 1.0 ml. of 6.5 N methanolic hydrochloric acid. The crystalline solid which formed was collected by filtration and identified as 1.82 g. of dl-trans-1-hydroxy-3-(1,1-dimethylheptyl)-6,6-dimethyl-9-(2-hydroxyethyl)amino-6a,7,8,9,10,10a-hexahydro-6H-dibenzo[b,d]pyran hydrochloride.

Analysis calc. for $C_{26}H_{44}NO_3Cl$: Theory: C, 68.77; H, 9.77; N, 3.08; Cl, 7.81. Found: C, 68.48; H, 9.58; N, 3.25; Cl, 7.51.

m/e: calc. 417; found 417.

EXAMPLE 21 dl-1-Hydroxy-3-(1,1-dimethylheptyl)-6,6-dimethyl-9-piperidino-6a,7,8,9,10,10a-hexahydro-6H-dibenzo[b,d]pyran Following the general procedure set forth in Example 20, 744 mg. of dl-1-hydroxy-3-(1,1-dimethylheptyl)-6,6-dimethyl-6a,7,8,9,10,10a-hexahydro-6H-dibenzo[b,d]pyran-9-one was reacted with 1.7 g. of piperidine to form the corresponding imine, which then was reduced by reaction with 190 mg. of sodium cyanoborohydride and 0.75 ml. of 6.5 N hydrochloric acid. Normal workup of the reaction mixture gave the product as an oil, which then was treated with methanolic hydrochloric acid to afford 689 mg. of crystalline dl-1-hydroxy-3-(1,1-dimethylheptyl)-6,6-dimethyl-9-piperidino-6a,7,8,9,10,10a-hexahydro-6H-dibenzo[b,d]pyran.

Analysis calc. for $C_{29}H_{48}NO_2Cl$: Theory: C, 72.85; H, 10.12; N, 2.93; Cl, 7.41. Found: C, 72.70; H, 10.12; N, 3.14; Cl, 7.16.

m/e: calc. 441; found 441.

EXAMPLE 22

The procedure of Example 20 was repeated using morpholine as the amine. Normal workup provided the product as an oil. The oil was reacted with hydrochloric acid in methanol to afford 615 mg. of dl-trans-1-hydroxy-3-(1,1-dimethylheptyl)-6,6-dimethyl-9-morpholino-6a,7,8,9,10,10a-hexahydro-6H-dibenzo[b,d]pyran hydrochloride.

Analysis calc. for $C_{28}H_{46}NO_3Cl$: Theory: C, 70.04; H, 9.66; N, 2.92; Cl, 7.38. Found: C, 69.79; H, 9.40; N, 3.04; Cl, 7.15.

m/e: calc. 443; found 443.

EXAMPLE 23 dl-trans-1-Hydroxy-3-(1,1-dimethylheptyl)-6,6-dimethyl-9-(3-hydroxcarbonyl)propionamido-6a,7,8,9,10,10a-hexahydro-6H-dibenzo[b,d]pyran A solution of 372 mg. of dl-trans-1-hydroxy-3-(1,1-dimethylheptyl)-6,6-dimethyl-9-amino-6a,7,8,9,10,10a-hexahydro-6H-dibenzo[b,d]pyran in 20 ml. of methanol containing 1.0 g. of succinic anhydride and 2.5 ml. of triethylamine was stirred at room temperature for seventy-two hours. The reaction mixture was then diluted with 50 ml. of water, and the organic solvent was removed by evaporation. The aqueous layer was extracted with diethyl ether, and the ethereal extracts were combined, washed with water, 2 N hydrochloric acid, again with water, and with 10 percent sodium bicarbonate. After drying the solution, the solvent was removed by evaporation under reduced pressure to afford the product as a foam. The foam was applied to a column packed with 20 g. of Woelm Activity No. 2 silica gel and eluted with ethyl acetate. Fractions shown by thin layer chromatography to contain the major component were combined and the solvent was evaporated therefrom to provide 507 mg. of dl-trans-1-hydroxy-3-(1,1-dimethylheptyl)-6,6-dimethyl-9-(3-hydroxycarbonyl)propionamido-6a,7,8,9,10,10a-hexahydro-6H-dibenzo[b,d]pyran.

Analysis calc. for $C_{28}H_{43}NO_5$: Theory: C, 71.00; H, 9.15; N, 2.96. Found: C, 70.98; H, 9.35; N, 2.97.

EXAMPLE 24 dl-trans-1-Hydroxy-3-(1,1-dimethylheptyl)-6,6-dimethyl-9-benzamido-6a,7,8,9,10,10a-hexahydro-6H-dibenzo[b,d]pyran To a solution of 373 mg. of dl-trans-1-hydroxy-3-(1,1-dimethylheptyl)-6,6-dimethyl-9-amino-6a,7,8,9,10,10a-hexahydro-6H-dibenzo[b,d]pyran in 20 ml. of methanol was added in one portion a solution of 2.26 g. of benzoic anhydride in 2.5 ml. of triethylamine. The reaction mixture was stirred for sixty hours at room temperature, and then was diluted with 20 ml. of water and stirred for an additional two hours. The organic solvent was removed by evaporation, and the aqueous phase was extracted with diethyl ether. The ethereal extracts were combined, washed with water, 2 N hydrochloric acid, again with water, and finally with 10 percent aqueous sodium bicarbonate. The organic layer was dried and the solvent was removed by evaporation to provide the product as a foam. The foam was chromatographed over 20 g. of Woelm activity No. 1 silica gel, eluting with fifty percent diethyl ether in hexane. The appropriate fractions were collected and the solvent was removed therefrom by evaporation to afford 525 mg. of dl-trans-1-hydroxy-3-(1,1-dimethylheptyl)-6,6-dimethyl-9-benzamido-6a,7,8,9,10,10a-hexahydro-6H-dibenzo[b,d]pyran.

Analysis calc. for $C_{30}H_{43}NO_3$: Theory: C, 77.95; H, 9.07; N, 2.93. Found: C, 77.75; H, 9.30; N, 2.91.

m/e: calc. 477; found 477.

EXAMPLE 25 dl-trans-1-Hydroxy-3-(1,2-dimethylheptyl)-6,6-dimethyl-9-hydroxyimino-6a,7,8,9,10,10a-hexahydro-6H-dibenzo[b,d]pyran To a stirred solution of 2.0 g. of dl-trans-1-hydroxy-3-(1,2-dimethylheptyl)-6,6-dimethyl-6a,7,8,9,10,10a-hexahydro-6H-dibenzo[b,d]pyran-9-one in 40 ml. of ethanol containing 10 ml. of water was added in one portion 560 mg. of hydroxylamine hydrochloride followed by the addition of 2 ml. of 5 N sodium hydroxide. The reaction mixture was heated to reflux and was stirred for ninety minutes. The reaction mixture was cooled and the ethanol was removed by evaporation. The aqueous layer was extracted with diethyl ether, and the ethereal extracts were combined, washed with water and dried. Removal of the solvent by evaporation under reduced pressure provided 2.3 g. of the product as an oil. The oil was purified by chromatography over 100 g. of silica gel, eluting with diethyl ether. The appropriate fractions were collected and the solvent was evaporated therefrom to provide 1.46 g. of dl-trans-1-hydroxy-3-(1,2-dimethylheptyl)-6,6-dimethyl-9-hydroxyimino-6a,7,8,9,10,10a-hexahydro-6H-dibenzo[b,d]pyran.

Analysis calc. for $C_{24}H_{37}NO_3$: Theory: C, 74.38; H, 9.62; N, 3.61. Found: C, 74.13; H, 9.50; N, 3.39.

m/e: calc. 387; found 387.

EXAMPLE 26

Following the procedure set forth in Example 25, 7.44 g. of dl-cis-1-hydroxy-3-(1,1-dimethylheptyl)-6,6-dimethyl-6a,7,8,9,10,10a-hexahydro-6H-dibenzo[b,d]pyran-9-one was reacted with 2.1 g. of hydroxylamine hydrochloride and 8 ml. of 5 N sodium hydroxide in 100 ml. of ethanol containing 25 ml. of water. Normal workup provided a foam which was crystallized from 75 ml. of hexane to provide 7.43 g. of dl-cis-1-hydroxy-3-(1,1-dimethylheptyl)-6,6-dimethyl-9-hydroxyimino-6a,7,8,9,10,10a-hexahydro-6H-dibenzo[b,d]pyran. M.P. 162°–164° C.

Analysis calc. for $C_{24}H_{37}NO_3$: Theory: C, 74.38; H, 9.62; N, 3.61. Found: C, 74.56; H, 9.41; N, 3.78

EXAMPLE 27 dl-trans-1-Hydroxy-3-(1,2-dimethylheptyl)-6,6-dimethyl-9-amino-6a,7,8,9,10,10a-hexahydro-6H-dibenzo[b,d]pyran A solution of 1.12 g. of dl-trans-1-hydroxy-3-(1,2-dimethylheptyl)-6,6-dimethyl-9-hydroxyimino-6a,7,8,9,10,10a-hexahydro-6H-dibenzo[b,d]pyran in 100 ml. of methanol containing 25 ml. of liquid ammonia and 1.0 g. of Raney nickel was stirred at 100° C. for eight hours under a hydrogen atmosphere of 1000 psi. The reaction mixture then was filtered and concentrated to a volume of about 50 ml., and then diluted with 25 ml. of ten percent sodium bicarbonate. The aqueous mixture was extracted with diethyl ether. The ethereal extracts were combined, washed with water, dried, and the solvent was evaporated therefrom to provide 861 mg. of dl-trans-1-hydroxy-3-(1,2-dimethylheptyl)-6,6-dimethyl-9-amino-6a,7,8,9,10,10a-hexahydro-6H-dibenzo[b,d]pyran.

Analysis calc. for $C_{24}H_{39}NO_2$: Theory: C, 77.16; H, 10.52; N, 3.75. Found: C, 77.54; H, 10.52; N, 3.94.

m/e: calc. 373; found 373.

EXAMPLE 28

Following the procedure set out in Example 27, 3.87 g. of dl-cis-1-hydroxy-3-(1,1-dimethylheptyl)-6,6-dimethyl-9-hydroxyimino-6a,7,8,9,10,10a-hexahydro-6H-dibenzo[b,d]pyran was hydrogenated by reaction with hydrogen (1000 psi) in the presence of 2.0 g. of Raney nickel in 100 ml. of methanol containing 25 ml. of liquid ammonia to provide 3.38 g. of dl-cis-1-hydroxy-3-(1,1-dimethylheptyl)-6,6-dimethyl-9-amino-6a,7,8,9,10,-10a-hexahydro-6H-dibenzo[b,d]pyran.

Analysis calc. for $C_{24}H_{39}NO_2$: Theory: C, 77.16; H, 10.52; N, 3.75. Found: C, 76.87; H, 10.44; N, 3.70.

m/e: calc. 373; found 373.

EXAMPLE 29 dl-trans-1-Hydroxy-3-(1,2-dimethylheptyl)-6,6-dimethy;-9-acetamido-6a,7,8,9,10,10a-hexahydro-6H-dibenzo[b,d]pyran A solution of 960 mg. of dl-trans-1-hydroxy-3-(1,2-dimethylheptyl)-6,6-dimethyl-9-amino-6a,7,8,9,10,10a-hexahydro-6H-dibenzo[b,d]pyran in 40 ml. of methanol containing 5 ml. of triethylamine and 5 ml. of acetic anhydride was stirred at room temperature for twenty-four hours. The methanol then was removed by evaporation, and the solution was diluted with 50 ml. of ten percent sodium bicarbonate and stirred for an additional two hours. The aqueous mixture was extracted with diethyl ether, and the ethereal extracts were combined, dried, and the solvent was removed to provide the product as a foam. The foam was chromatographed over 50 g. of silica gel, eluting first with 600 ml. of chloroform, 1000 ml. of one-half percent methanol in chloroform, then with 2000 ml. of one percent methanol in chloroform, and finally with 500 ml. of two percent methanol in chloroform. Fractions containing 20 ml. each were collected. Fractions 61–95 were combined and evaporated to dryness to provide 354 mg. of dl-trans-1-hydroxy-3-(1,2-dimethylheptyl)-6,6-dimethyl-9$\beta$-acetamido-6a,7,8,9,10,10a-hexahydro-6H-dibenzo[b,d]pyran. M.P. 140°–145° C.

Analysis calc. for $C_{26}H_{41}NO_3$: Theory: C, 75.14; H, 9.94; N, 3.37. Found: C, 74.91; H, 9.93; N, 3.53.

Fractions 101–150 were collected and the solvent was evaporated therefrom to provide 591 mg. of dl-trans-(1,2-dimethylheptyl)-6,6-dimethyl-9$\alpha$-acetamido-6a,7,8,9,10,10a-hexahydro-6H-dibenzo[b,d]pyran.

Analysis calc. for $C_{26}H_{41}NO_3$: Theory: C, 75.14; H, 9.94; N, 3.37. Found: C, 74.89; H, 9.65; N, 3.61.

EXAMPLE 30

Following the procedure set out in Example 29, 1.18 g. of dl-cis-1-hydroxy-3-(1,1-dimethylheptyl)-hexahydro-6H-dibenzo[b,d]pyran was acylated by reaction with acetic anhydride and triethylamine in methanol to provide, after chromatography, 545 mg. of dl-cis-1-hydroxy-3-(1,1-dimethylheptyl)-6,6-dimethyl-9$\beta$-acetamido-6a,7,8,9,10,10a-hexahydro-6H-dibenzo[b,d]pyran, M.P. 107°–120° C.; and 494 mg. of dl-cis-1-hydroxy-3-(1,1-dimethylheptyl)-6,6-dimethyl-9$\alpha$-acetamido-6a,7,8,9,10,10a-hexahydro-6H-dibenzo[b,d]pyran, M.P. 164°–168° C.

EXAMPLE 31 trans-1-Hydroxy-3-(1,1-dimethylheptyl)-6,6-dimethyl-9-N-(2-acetoxyethyl)acetamido-6a,7,8,9,10,10a-hexahydro-6H-dibenzo[b,d]pyran A solution of 500 mg. of trans-1-hydroxy-3-(1,1-dimethylheptyl)-6,6-dimethyl-9-(2-hydroxyethyl)amino-6a,7,8,9,10,10a-hexahydro-6H-dibenzo[b,d]pyran hydrochloride, prepared as described in Example 20, in 25 ml. of methanol containing 1.5 ml. of triethylamine and 1.5 ml. of pyridine was stirred at 25° C. for forty-eight hours. The reaction mixture then was diluted with 50 ml. of chloroform, and the diluted solution was heated at reflux for twenty-four hours. The reaction mixture was cooled to room temperature and the solvent was evaporated therefrom to afford trans-1-hydroxy-3-(1,1-dimethylheptyl)-6,6-dimethyl-9-N-(2-acetoxyethyl)acetamido-6a,7,8,9,10,10a-hexahydro-6H-dibenzo[b,d]pyran.

Analysis calc. for $C_{30}H_{47}NO_5$: Theory: C, 71.82; H, 9.44; N, 2.79. Found: C, 69.46; H, 8.72; N, 2.56.

m/e: calc. 501; found 501.

EXAMPLE 32 trans-1-Hydroxy-3-(1,1-dimethylheptyl)-6,6-dimethyl-9-N-(2-hydroxyethyl)acetamido-6a,7,8,9,10,10a-hexahydro-6H-dibenzo[b,d]pyran A solution of 500 mg. of trans-1-hydroxy-3-(1,1-dimethylheptyl)-6,6-dimethyl-9-N-(2-acetoxyethyl)acetamido-6a,7,8,9,10,10a-hexahydro-6H-dibenzo[b,d]pyran from Example 31 was dissolved in a solution of 40 ml. of methanol and 10 ml. of water containing 138 mg. of potassium carbonate. The reaction mixture was stirred at 25° C. for ninety minutes, and then was diluted with 150 ml. of saturated aqueous sodium chloride solution. The aqueous mixture was extracted several times with diethyl ether. The ethereal extracts were combined, washed with water, dried, and the solvent was removed by evaporation under reduced pressure to provide 500 mg. of the prodict as a white solid. The solid thus formed was crystallized from a mixture of cyclohexane, hexane and ethyl acetate to afford 395 mg. of trans-1-hydroxy-3-(1,1-dimethylheptyl)-6,6-dimethyl-9-N-(2-hydroxyethyl)acetamido-6a,7,8,9,10,10a-hexahydro-6H-dibenzo[b,d]pyran. M.P. 148°–158° C.

m/e: 459

Analysis calc. for $C_{28}H_{45}NO_4$: Theory: C, 73.16; H, 9.87; N, 3.05. Found: C, 73.05; H, 9.84; N, 3.15.

EXAMPLE 33 dl-trans-1-Hydroxy-3-(1,1-dimethylheptyl)-6,6-dimethyl-9-N-(acetoxy)acetamido-6a,7,8,9,10,10a-hexahydro-6H-dibenzo[b,d]pyran A solution of 2.5 ml. of acetic anhydride in 25 ml. of methanol containing 500 mg. of dl-trans-1-hydroxy-3-(1,1-dimethylheptyl)-6,6-dimethyl-9-hydroxyamino-6a,7,8,9,10,10a-hexahydro-6H-dibenzo[b,d]pyran (prepared according to Example 2) was stirred at 25° C. for twenty-four hours. The solvent was then removed by evaporation, and the residual oil was dissolved in diethyl ether and washed with dilute aqueous sodium bicarbonate solution. The ethereal layer was dried, and the solvent was evaporated therefrom to afford 550 mg. of the product as a foam. The foam was crystallized from 20 ml. of hexane to afford 230 mg. of dl-trans-1-hydroxy-3-(1,1-dimethylheptyl)-6,6-dimethyl-9-N-(acetoxy)acetamido-6a,7,8,9,10,10a-hexahydro-6H-dibenzo[b,d]pyran. M.P. 153°–155° C. A second crop of crystalline product afforded 167 mg. M.P. 133°–135° C. The two crops of crystalline product were combined and analyzed.

Analysis calc. for $C_{28}H_{43}NO_5$: Theory: C, 71.00; H, 9.15; N, 2.96. Found: C, 71.21; H, 8.95; N, 3.06.

m/e: calc. 473; found 473.

EXAMPLE 34 dl-trans-1-Hydroxy-3-(1,1-dimethylheptyl)-6,6-dimethyl-9-N-(2-propyn-1-yl)acetamido-6a,7,8,9,10,10a-hexahydro-6H-dibenzo[b,d]pyran To a stirred solution of 500 mg. of dl-trans-1-hydroxy-3-(1,1-dimethylheptyl)-6,6-dimethyl-9-(2-propyn-1-yl)amino-6a,7,8,9,10,10a-hexahydro-6H-dibenzo[b,d]pyran in 25 ml. of methanol containing 1.5 ml. of triethylamine was added 1.5 ml. of acetic anhydride dropwise over five minutes. Following the complete addition, the reaction mixture was stirred at 25° C. for two days. The reaction solvent was then removed by evaporation, and the oil thus formed was dissolved in diethyl ether and washed with aqueous sodium bicarbonate. The ethereal solution was dried and the solvent then was removed to afford 500 mg. of the product as an oil. The oil was purified by chromatography over 25 g. of Woelm Activity I silica gel, eluting with diethyl ether. The appropriate fractions were collected and concentrated to dryness to provide 430 mg. of dl-trans-1-hydroxy-3-(1,1-dimethylheptyl)-6,6-dimethyl-9-N-(2-propyn-1-yl)acetamido-6a,7,8,9,10,10a-hexahydro-6H-dibenzo[b,d]pyran.

Analysis calc. for $C_{29}H_{44}NO_3$: Theory: C, 76.50; H, 9.40; N, 3.19. Found: C, 75.60; H, 9.18; N, 3.28.

m/e: calc. 453; found 453.

EXAMPLE 35 dl-trans-1-Hydroxy-3-(1,1-dimethylheptyl)-6,6-dimethyl-9-(N,N-dimethyl-N-propargyl)ammonium-6a,7,8,9,10,10a-hexahydro-6H-dibenzo[b,d]pyran bromide A solution of 600 mg. of dl-trans-1-hydroxy-3-(1,1-dimethylheptyl)-6,6-dimethyl-9-amino-6a,7,8,9,10,10a-hexahydro-6H-dibenzo[b,d]pyran in 25 ml. of ethanol containing 1.5 ml. of propargyl bromide was heated to reflux and stirred for forty-eight hours. The reaction mixture then was cooled to room temperature and concentrated to a volume of about 5 ml. The mixture was diluted with diethyl ether and hexane, whereupon the product precipitated. The precipitate was collected by filtration and shown to be 625 mg. of dl-trans-1-hydroxy-3-(1,1-dimethylheptyl)-6,6-dimethyl-9-(N,N-dimethyl-N-propargyl)ammonium-6a,7,8,9,10,10a-hexahydro-6H-dibenzo[b,d]pyran bromide.

Analysis calc. for $C_{29}H_{47}BrNO_2$: Theory: C, 66.39; H, 8.76; N, 2.77; Br, 15.77. Found: C, 65.45; H, 8.42; N, 2.66; Br, 14.94.

EXAMPLE 36

6aR,10aR-trans-1-Hydroxy-3-(1,1-dimethylheptyl)-6,6-dimethyl-9R (and 9S) acetamido-6a,7,8,9,10,10a-hexahydro-6H-dibenzo[b,d]pyran Following the general procedure set out in Example 1, 7.5 g. of 6aR,10aR-trans-1-Hydroxy-3-(1,1-dimethylheptyl)-6,6-dimethyl-6a,7,8,9,10,10a-hexahydro-6H-dibenzo[b,d]pyran-9-one was reacted with 2.1 g. of hydroxylamine to provide the corresponding optically active oxime. The oxime so formed was reduced by reaction with hydrogen in the presence of Raney nickel to provide 1.49 g. of a mixture of 6aR,10aR-trans-1-hydroxy-3-(1,1-dimethylheptyl)-6,6-dimethyl-9R (and 9S) amino-6a,7,8,9,10,10a-hexahydro-6H-dibenzo[b,d]pyran. A solution of the latter compound in 35 ml. of methanol containing 10 ml. of triethylamine was stirred at 25° C. while 5 ml. of acetic anhydride was added dropwise over ten minutes. The reaction mixture then was stirred at room temperature for seventy-two hours, after which time the solvent was removed by evaporation under reduced pressure. The residual oil was next dissolved in 50 ml. of diethyl ether containing 10 ml. of water. The aqueous ethereal solution was stirred for two hours at room temperature, and then the organic layer was separated, washed with aqueous sodium bicarbonate and dried. Evaporation of the solvent provided 1.52 g. of a white foam. The product thus formed was chromatographed twice over columns packed with 100 g. of Woelm Activity I silica gel and eluted with 600 ml. of chloroform, 1000 ml. of one-half percent by volume of methanol in chloroform, and finally with one percent methanol in chloroform. Fractions containing 20 ml. each were collected. Fractions shown by thin layer chromatographic analysis to consist of one component were combined and the solvent was removed therefrom by evaporation under reduced pressure to provide 287 mg. of 6aR,10aR-trans-1-hydroxy-3-(1,1-dimethylheptyl)-6,6-dimethyl-9R-acetamido-6a,7,8,9,10,10a-hexahydro-6H-dibenzo[b,d]pyran.

Analysis calc. for $C_{26}H_{41}NO_3$: Theory: C, 75.14; H, 9.94; N, 3.37. Found: C, 75.32; H, 9.77; N, 3.12.

m/e: calc. 415; found 415.

$[\alpha]_D^{CHCl_3} - 1.2°$; $[\alpha]_{365}^{CHCl_3} + 29.9°$.

Further chromatographic separation provided fractions containing 591 mg. of 6aR,10aR,-trans-1-hydroxy-3-(1,1-dimethylheptyl)-6,6-dimethyl-9S-acetamido-6a,7,8,9,10,10a-hexahydro-6H-dibenzo[b,d]pyran.

Analysis calc. for $C_{26}H_{41}NO_3$: Theory: C, 75.14; H, 9.94; N, 3.37. Found: C, 74.91; H, 9.99; N, 3.18.

m/e: calc. 415; found 415.

$[\alpha]_D^{CHCl_3} - 64.9°$; $[\alpha]_{365}^{CHCl_3} - 236.5°$.

EXAMPLE 37

A parenteral composition suitable for administration by injection is prepared by dissolving 25 mg. of dl-trans-1-hydroxy-3-(1,2-dimethylheptyl)-6,6-dimethyl-9-(N-ethyl)acetamido-6a,7,8,9,10,10a-hexahydro-6H-dibenzo[b,d]pyran in 250 ml. of 0.9 percent aqueous sodium chloride solution and adjusting the pH of the solution to between 6 and 7.

EXAMPLE 38

An aqueous suspension suitable for oral administration is prepared by admixing 10 mg. of finely divided dl-trans-1-hydroxy-3-(1-ethyl-2-hexenyl)-9-hydroxyimino-6a,7,8,9,10,10a-hexahydro-6H-dibenzo[b,d]pyran with 500 mg. of acacia, 5 mg. of sodium benzoate; 1.0 g. of sorbitol solution, U.S.P., 5 mg. of sodium saccharin, and 0.025 ml. of vanilla tincture.

We claim:

1. A pharmaceutical formulation useful in lowering blood pressure comprising a hypotensively effective amount of a 9-amino-dibenzo[b,d]pyran of the formula

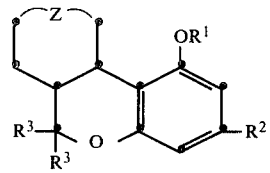

wherein:
$R^1$ is hydrogen or $C_1-C_4$ alkanoyl;
$R^2$ is $C_5-C_{10}$ alkyl or $C_5-C_{10}$ alkenyl;
$R^3$ is hydrogen or methyl; and
Z is selected from the group consisting of

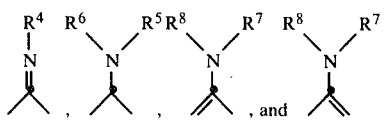

wherein:
$R^4$ is hydroxy, $C_1-C_4$ alkoxy, or $C_1-C_7$ alkanoyloxy;
$R^5$ taken singly is hydrogen, hydroxy, $C_1-C_4$ alkoxy, $C_1-C_4$ alkyl, $CH_2C_2-C_4$ alkenyl, $CH_2C_2-C_4$ alkynyl, $C_1-C_7$ alkanoyl, $C_1-C_7$ alkanoyloxy, phenyl- $C_1$–$C_2$ alkyl, phenyl-$C_1$–$C_2$ alkanoyl, —(CH$_2$)$_n$—OH, —(CH$_2$)$_n$—O—$C_1$—$C_2$ alkanoyl, $$-\overset{O}{\underset{\|}{C}}-(CH_2)_n COOH,$$

wherein n is 2, 3 or 4;
$R^6$ taken singly is hydrogen, $C_1$-$C_4$ alkyl, CH$_2$C$_2$-$C_4$ alkenyl, CH$_2$C$_2$-$C_4$ alkynyl, $C_1$-$C_7$ alkanoyl, phenyl-$C_1$-$C_2$ alkyl or phenyl-$C_1$-$C_2$ alkanoyl;
$R_5$ and $R_6$ taken together with the nitrogen to which they are attached complete a heterocyclic ring selected from pyrrolidine, 2-oxopyrrolidine, 2,5-dioxopyrrolidine, piperidine, 2-oxopiperidine, 2,6-dioxopiperidine and morpholine;
$R^7$ taken singly is hydrogen, $C_1$-$C_7$ alkanoyl, phenyl-$C_1$-$C_2$ alkanoyl or $$-\overset{O}{\underset{\|}{C}}(CH_2)_n COOH,$$

wherein n is 2, 3 or 4;
$R^8$ taken singly is $C_1$-$C_7$ alkanoyl or phenyl-$C_1$-$C_2$ alkanoyl;
$R^7$ and $R^8$ taken together with the nitrogen to which they are attached complete a heterocyclic ring selected from 2-oxopyrrolidine, 2,5-dioxopyrrolidine, 2-oxopiperidine and 2,6-dioxopiperidine;
and the non-toxic pharmaceutically acceptable acid addition salts and quaternary ammonium salts thereof, is association with a pharmaceutically acceptable diluent or carrier therefor.

2. The pharmaceutical formulation according to claim 1 wherein the active ingredient is a compound of the formula

[chemical structure]

wherein:
$R^1$ is hydrogen or $C_1$-$C_4$ alkanoyl;
$R^2$ is $C_5$-$C_{10}$ alkyl or $C_5$-$C_{10}$ alkenyl;
$R^3$ is hydrogen or methyl; and
Z is selected from the group consisting of

[chemical structures]

wherein:
$R^5$ is hydrogen, $C_1$-$C_7$ alkanoyl, phenyl-$C_1$-$C_2$ alkanoyl, or $$-\overset{O}{\underset{\|}{C}}-(CH_2)_n COOH$$

wherein n is 2, 3 or 4;
$R^6$ is $C_1$-$C_7$ alkanoyl or phenyl-$C_1$-$C_2$ alkanoyl;
$R^7$ is hydrogen, $C_1$-$C_7$ alkanoyl, phenyl-$C_1$-$C_2$ alkanoyl or $$-\overset{O}{\underset{\|}{C}}-(CH_2)_n COOH;$$

and $R^8$ is $C_1$-$C_7$ alkanoyl or phenyl-$C_1$-$C_2$ alkanoyl.

3. The formulation according to claim 2 wherein Z is

[chemical structure]

4. The formulation according to claim 3 wherein $R^5$ is hydrogen.

5. The formulation according to claim 4 wherein $R^6$ is $C_1$-$C_7$ alkanoyl.

6. The formulation according to claim 4 wherein $R^6$ is $C_1$-$C_4$ alkanoyl.

7. The formulation according to claim 6 wherein $R^6$ is acetyl.

8. The formulation according to claim 6 wherein in the active ingredient,
$R^1$ is hydrogen;
$R^2$ is $C_5$-$C_{10}$ alkyl; and
$R^3$ is methyl.

9. The formulation according to claim 8 wherein the active ingredient is dl-6a,10a-trans-1-hydroxy-3-(1,1-dimethylheptyl)-6,6-dimethyl-9-acetamido-6a,7,8,9,10,-10a-hexahydro-6H-dibenzo[b,d]pyran.

10. A method of treating hypertension in mammals comprising administering to a subject suffering from high blood pressure and in need of treatment or to a subject suspected of developing high blood pressure a hypotensively effective dose of a compound of the formula

[chemical structure]

wherein:
$R^1$ is hydrogen or $C_1$-$C_4$ alkanoyl;
$R^2$ is $C_5$-$C_{10}$ alkyl or $C_5$-$C_{10}$ alkenyl;
$R^3$ is hydrogen or methyl; and
Z is selected from the group consisting of

[chemical structures]

wherein:
$R^4$ is hydroxy, $C_1$-$C_4$ alkoxy, or $C_1$-$C_7$ alkanoyloxy;
$R^5$ taken singly is hydrogen, hydroxy, $C_1$-$C_4$ alkoxy, $C_1$-$C_4$ alkyl, CH$_2$C$_2$-$C_4$ alkenyl, CH$_2$C$_2$-$C_4$ alkynyl, $C_1$-$C_7$ alkanoyl, $C_1$-$C_7$ alkanoyloxy, phenyl-$C_1$-$C_2$ alkyl, phenyl-$C_1$-$C_2$ alkanoyl, —(CH$_2$)$_n$—OH, —(CH$_2$)$_n$—O—$C_1$—$C_2$ alkanoyl, $$-\overset{O}{\underset{\|}{C}}-(CH_2)_n COOH,$$

wherein n is 2, 3 or 4;

R⁶ taken singly is hydrogen, $C_1$-$C_4$ alkyl, $CH_2C_2$-$C_4$ alkenyl, $CH_2C_2$-$C_4$ alkynyl, $C_1$-$C_7$ alkanoyl, phenyl-$C_1$-$C_2$ alkyl or phenyl-$C_1$-$C_2$ alkanoyl;

R₅ and R₆ taken together with the nitrogen to which they are attached complete a heterocyclic ring selected from pyrrolidine, 2-oxopyrrolidine, 2,5-dioxopyrrolidine, piperidine, 2-oxopiperidine, 2,6-dioxopiperidine and morpholine;

R⁷ taken singly is hydrogen, $C_1$-$C_7$ alkanoyl, phenyl-$C_1$-$C_2$ alkanoyl or $$-\overset{O}{\underset{\|}{C}}(CH_2)_n COOH,$$

wherein n is 2, 3 or 4;

R⁸ taken singly is $C_1$-$C_7$ alkanoyl or phenyl-$C_1$-$C_2$ alkanoyl;

R⁷ and R⁸ taken together with the nitrogen to which they are attached complete a heterocyclic ring selected from 2-oxopyrrolidine, 2,5-dioxopyrrolidine, 2-oxopiperidine and 2,6-dioxopiperidine;

and the non-toxic pharmaceutically acceptable acid addition salts and quaternary ammonium salts thereof.

11. The method of treatment according to claim 10 wherein the compound administered has the formula wherein:
R¹ is hydrogen or $C_1$-$C_4$ alkanoyl;
R² is $C_5$-$C_{10}$ alkyl or $C_5$-$C_{10}$ alkenyl;
R³ is hydrogen or methyl; and
Z is selected from the group consisting of wherein:
R⁵ is hydrogen, $C_1$-$C_7$ alkanoyl, phenyl-$C_1$-$C_2$ alkanoyl, or $$-\overset{O}{\underset{\|}{C}}-(CH_2)_n COOH;$$

wherein n is 2, 3 or 4;
R⁶ is $C_1$-$C_7$ alkanoyl or phenyl-$C_1$-$C_2$ alkanoyl;
R⁷ is hydrogen, $C_1$-$C_7$ alkanoyl, phenyl-$C_1$-$C_2$ alkanoyl or $$-\overset{O}{\underset{\|}{C}}-(CH_2)_n-COOH;$$

and
R⁸ is $C_1$-$C_7$ alkanoyl or phenyl-$C_1$-$C_2$ alkanoyl.

12. The method according to claim 11 wherein in the compound administered, R¹ is hydrogen;
R² is $C_5$-$C_{10}$ alkyl;
R³ is methyl.

13. The method according to claim 12 wherein in the compound administered, Z is

14. The method according to claim 13 wherein in the compound administered, R⁵ is hydrogen.

15. The method according to claim 14 wherein in the compound administered, R⁶ is $C_1$-$C_7$ alkanoyl.

16. The method according to claim 15 wherein in the compound administered, R⁶ is $C_1$-$C_2$ alkanoyl.

17. The method according to claim 16 wherein the compound administered is dl-6a,10a-trans-1-hydroxy-3-(1,1-dimethylheptyl)-6,6-dimethyl-9-acetamido-6a,7,8,9,10,10a-hexahydro-6H-dibenzo[b,d]pyran.

18. The method according to claim 16 wherein the compound administered is 6aR,10aR-trans-1-hydroxy-3-(1,1-dimethylheptyl)-6,6-dimethyl-9R-acetamido-6a,7,8,9,10,10a-hexahydro-6H-dibenzo[b,d]pyran.

* * * * *